(12) United States Patent
      Ghosh

(10) Patent No.: US 12,661,076 B2
(45) Date of Patent: Jun. 23, 2026

(54) DETERMINING PANCREAS DISEASE USING FUNCTIONAL IMAGING

(71) Applicant: Hepatiq, Inc., Irvine, CA (US)

(72) Inventor: Dipankar Ghosh, Irvine, CA (US)

(73) Assignee: Hepatiq, Inc., Irvine, CA (US)

( * ) Notice:   Subject to any disclaimer, the term of this patent is extended or adjusted under 35 U.S.C. 154(b) by 99 days.

(21) Appl. No.: 19/088,789

(22) Filed:      Mar. 24, 2025

(65)              Prior Publication Data

US 2025/0302409 A1      Oct. 2, 2025

Related U.S. Application Data

(60) Provisional application No. 63/570,077, filed on Mar. 26, 2024.

(51) Int. Cl.
   *A61B 6/40*       (2024.01)
   *A61B 6/00*       (2024.01)
   *A61B 6/50*       (2024.01)
   *G06T 7/00*       (2017.01)
   *G06T 7/62*       (2017.01)

(52) U.S. Cl.
   CPC .............. *A61B 6/4057* (2013.01); *A61B 6/50* (2013.01); *A61B 6/5205* (2013.01); *G06T 7/0012* (2013.01); *G06T 7/62* (2017.01)

(58) Field of Classification Search
   CPC ..... G06T 7/0012; G06T 7/62; A61B 6/45057; A61B 6/50; A61B 6/5205
   See application file for complete search history.

(56)                  References Cited

U.S. PATENT DOCUMENTS

| | | | |
|---|---|---|---|
| 9,155,513 B2 | 10/2015 | Ghosh et al. | |
| 10,076,299 B2 | 9/2018 | Ghosh et al. | |
| 11,615,881 B2 | 3/2023 | Ghosh et al. | |
| 12,009,090 B2 | 6/2024 | Ghosh et al. | |
| 2015/0025372 A1* | 1/2015 | Ghosh ................... | G06T 7/0014 |
| | | | 600/431 |
| 2022/0049011 A1* | 2/2022 | Engle ................ | C07K 16/2896 |

OTHER PUBLICATIONS

Rassam, F. "Practical guidelines for the use of technetium-99m mebrofenin hepatobiliary scintigraphy in the quantitative assessment of liver function". Nuclear Medicine Communications, 40:297-307, 2019 (Year: 2019).*

(Continued)

*Primary Examiner* — Keith M Raymond
*Assistant Examiner* — Milton Truong
(74) *Attorney, Agent, or Firm* — Michael J. Bolan; Vista IP Law Group, LLP

(57)                  ABSTRACT

A diagnostic system for determining a health condition of an organ of a patient that has been administered a radioisotope dose uptaken by the organ, comprises at least one processor configured for receiving image data acquired from the patient when the radioisotope dose is active in the patient, analyzing the received image data to determine a functional organ volume index and an individual organ function index, staging a health of the organ based on the determined functional organ volume index and the determined individual organ function index. The diagnostic system further comprises a user interface device configured for communicating the staged health of the organ to a clinician.

20 Claims, 20 Drawing Sheets

(56)     References Cited

OTHER PUBLICATIONS

Chapelle, T. et al. "Future remnant liver function estimated by combining liver volumetry on magnetic resonance imaging with total liver function on 99mTc-mebrofenin hepatobiliary scintigraphy: can this tool predict post-hepatectomy liver failure?". HPB, 18, 494-503, 2016 (Year: 2016).*

De Graff, W. et al. "Assessment of Future Remnant Liver Function Using Hepatobiliary Scintigraphy in Patients Undergoing Major Liver Resection". J Gastrointest Surg, 14:369-378, 2010 (Year: 2010).*

Moreno-Osset, E. et al. "99mTc-Hexamethylpropylene Amineoxime Leukocyte Scintigraphy in Acute Pancreatitis: An Alternative to Contrast-Enhanced Computed Tomography?". Am J Gastroenterol, 100:153-161, 2005 (Year: 2005).*

* cited by examiner

Fig. 13
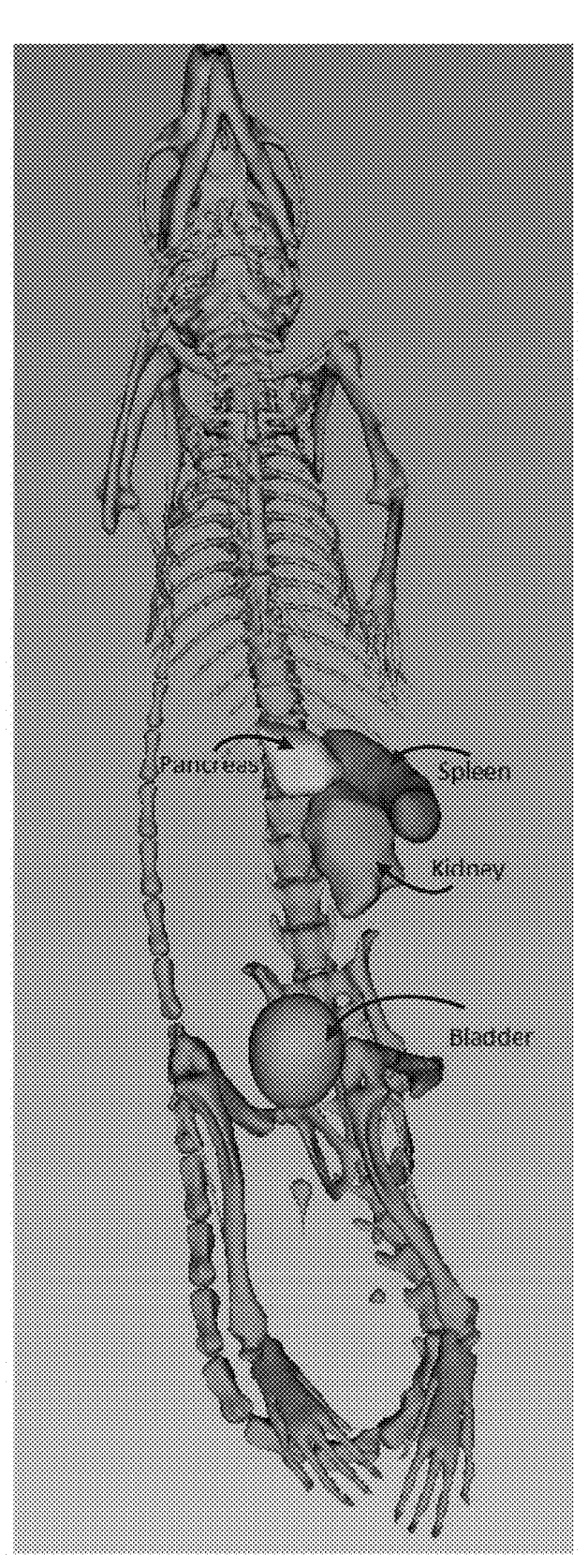

Fig. 15

| | Pancreas Function (PF) Index | | | Functional Pancreas Volume (fPV) Index | | |
|---|---|---|---|---|---|---|
| | Baseline | Post Cerulein | ΔPF | Baseline | Post Cerulein | ΔfPV |
| Mouse 2A | 0.88 | 0.28 | -69% | 0.81 | 0.64 | -21% |
| Mouse 3A | 1.12 | 0.03 | -97% | 1.12 | 0.51 | -54% |
| Mouse 4A | 0.98 | 0.23 | -77% | 1.07 | 0.45 | -58% |
| Mean= | 1.00 | 0.18 | -82% | 1.00 | 0.53 | -47% |
| StDev= | 0.12 | 0.13 | | 0.16 | 0.10 | |

Figure 18:
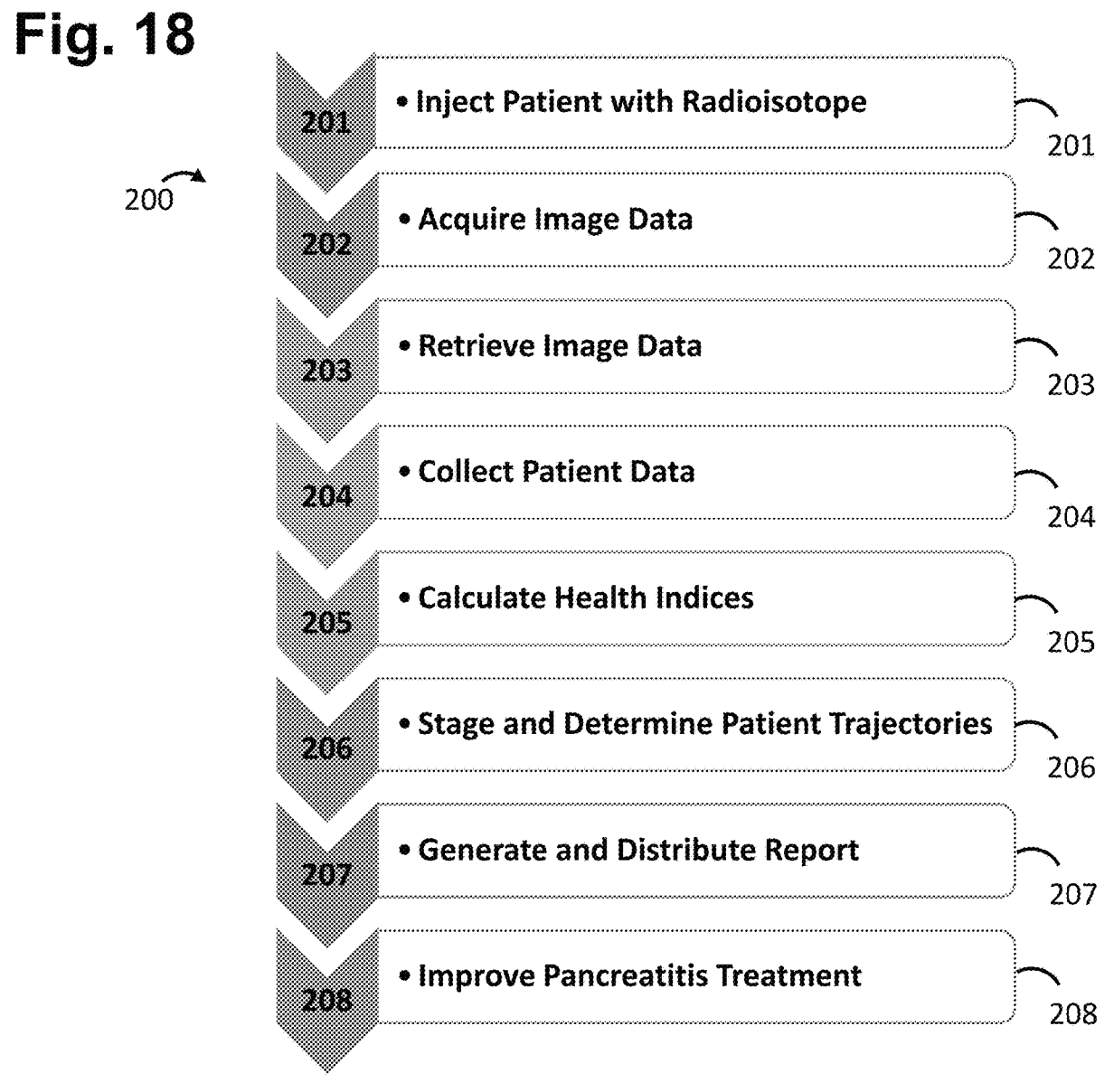

- Inject Patient with Radioisotope — 201
- Acquire Image Data — 202
- Retrieve Image Data — 203
- Collect Patient Data — 204
- Calculate Health Indices — 205
- Stage and Determine Patient Trajectories — 206
- Generate and Distribute Report — 207
- Improve Pancreatitis Treatment — 208

201  202  203  204  205  206  207  208

DETERMINING PANCREAS DISEASE USING FUNCTIONAL IMAGING

RELATED APPLICATION

This application claims the benefit of U.S. Provisional Application No. 63/570,077 titled "DETERMINING PANCREAS DISEASE USING FUNCTIONAL IMAGING," filed Mar. 26, 2024, which is incorporated herein by reference in its entirety.

FIELD

The present disclosure relates generally to diagnostic imaging, and more particularly, to nuclear medicine imaging of an organ of a patient.

BACKGROUND

The pancreas is a gland located behind the stomach and next to the small intestine. It has two main functions. The endocrine part makes the hormones insulin and glucagon and releases them directly into the bloodstream to control sugar levels. The exocrine part makes enzymes and releases them through ducts to help break down proteins, fats, and carbohydrates for absorption in the intestine.

Acute pancreatitis is inflammation of the pancreas commonly due to biliary obstruction that causes swelling and pain. Acute pancreatitis occurs quickly and has mortality of about 10%. In the USA, there are more than 300,000 hospitalizations per year for acute pancreatitis, with costs of $2+ billion (see National Pancreas Foundation, https://pancreasfoundation.org/). Chronic pancreatitis (CP) is a progressive disease characterized by inflammation, dysfunction, and fibrosis. It is associated with alcohol use, smoking, gene mutations, biliary obstruction, viral disease, and immune system activity. CP begins with recurrent bouts of acute pancreatitis, followed by chronic pain. CP results in fibrosis and scarring that damage the pancreas, and may cause serious long-term complications, including pseudocyst formation, splenic venous thrombosis, pancreatic ascites, pleural effusion, pseudoaneurysms, diabetes, metabolic bone disease and pancreatic cancer. 86,000 hospital admissions annually are attributed to CP in the United States alone. The 10 year mortality is 30%, rising to 55% at 20 years. CP incidence is growing due to lifestyle and food habits.

In the basal state, the pancreas excrete small amounts of protein-rich fluid. During a meal, gastric distension and acid production stimulate the duodenal "S" cells to release the hormone secretin into the blood, which signals the pancreatic ductal cells to secrete bicarbonate-rich fluid. Similarly, the postprandial increase in amino and fatty acids stimulates the duodenal "I" cells to release the hormone cholecystokinin (CCK), which signals the pancreatic acinar cells to secrete enzyme-rich fluid. With CP, pancreas production shows decreased fluid volume, bicarbonate and enzymes in response to secretin and CCK compared to the normal pancreas.

Diagnosis of chronic pancreatis is difficult, and treatments are therefore delayed since the pancreas is relatively inaccessible. To make matters worse, because the symptoms are similar, CP may initially be confused with acute pancreatis. Although several tests are available for diagnosing pancreatic diseases based on the detection of abnormal function or structure of the pancreas (see, e.g., Peter V. Draganov, "*Pancreatic function testing: Here to stay for the 21st*

*century,*" World Journal of Gastroenterology, 2008 May 28; 14 (20): 3149-3158), such tests are inadequate.

Pancreas health can be assessed directly by measuring electrolytes and enzymes in pancreas fluid or indirectly by measuring fecal elastase or trypsinogen in the blood.

Direct function tests (e.g., a secretin stimulation test (SST), a cholecystokinin (CCK) stimulation test (CST), a secretin-CCK stimulation test (SCST), perfusion testing, an intraductal stimulation secretin test (IDST), and an endoscopic secretin stimulation test (eSST)), may detect early CP, but have not been widely adopted due to invasiveness (patient intolerance) and complexity. For example, SST measures bicarbonate production by the pancreas. It requires the placement of a double lumen oral-duodenal tube through the mouth. A bolus of intravenous secretin is administered and duodenal fluid collected over one hour. Although highly accurate, the SST is invasive and takes a long time to perform. A CST measures enzyme production by the pancreas. It uses CCK infusion for stimulation rather than secretin. It also requires the placement of tubes through the mouth. Duodenal fluid is collected typically over about an hour and a half. Although highly accurate, the CST is invasive and takes a long time. An SCST measures both bicarbonate and enzyme production by the pancreas. This test has the advantage of simultaneous measurement of both functions but suffers from the same problems as the SST. Perfusion testing measures pancreatic enzyme activity in the duodenum. A standardized meal is used rather than CCK for stimulation. Volume of both gastric and duodenal collections are recorded over a three hour period. The inconvenience and time required for this test render it useful only for research. An IDST requires patient sedation and cannulation of the pancreatic duct. Pancreatic fluid is collected after the administration of secretin. This is a research tool that has not shown performance superior to SST. An eSST is similar to SST except that the patient is sedated and the biopsy channel of an endoscope used to collect duodenal secretions. It suffers from the same problems as the SST.

Fecal elastase tests (e.g., a fecal fat test, fecal chymotrypsin test, and fecal elastase (FE) test) and serum trypsin tests are simple, non-invasive, and can be performed on an outpatient basis, but they tend to perform poorly in patients with early CP as mischaracterization of any fecal elastase or trypsin abnormality as pancreatic dysfunction has led to over-diagnosis and over-treatment. Thus, these tests are reliable only for detecting advanced CP with steatorrhea. For example, the fecal fat test involves controlling diet and collecting stool for 72 hours and analyzing the contents. This is not practical and used generally for research purposes only. Spot fecal fat is another fecal test that has some value but is not sensitive for CP. In the fecal chymotrypsin test, chymotrypsin, made by the pancreas, is a useful stool marker. However, the fecal chymotrypsin assay is of little clinical value to detect early CP. The FE test suffers from the same limitations as the fecal chymotrypsin assay, notably that it only detects patients with steatorrhea and severe CP. A serum trypsin assay, like the fecal assays, is basically a marker of advanced CP and steatorrhea.

In contrast to functional tests, radiographic imaging (e.g., ultrasound (US), endoscopic ultrasound (EUS), endoscopic retrograde cholangio-pancreatography (ERCP), computed tomography (CT), and magnetic resonance cholangio-pancreatography (MRCP), and secretin-stimulated MRCP (s-MRCP)) are designed to detect abnormal structure in the pancreas. Radiographic imaging can provide accurate diagnosis of CP when ductal and parenchymal effects of fibrosis are evident. However, radiographic imaging do not directly measure dysfunction resulting from cellular abnormalities, and it is the cumulative effect of those cellular abnormalities that lead to advanced fibrotic changes. By the time such advanced fibrotic changes are visible to radiographic imaging, much of the pancreas may have become non-functional. Thus, these imaging techniques can detect only late stage CP, often when 50% or more of the pancreas has become fibrotic or has been essentially destroyed. In fact, a 2017 study indicated that, although these imaging techniques have good specificity (≥0.90) with respect to CP, they have poor sensitivity (≤0.82) (see Issa, Y., et al., "*Diagnostic performance of imaging modalities in chronic pancreatitis: a systematic review and meta-analysis,*" Eur Radiol, 2017. 27(9): p. 3820-3844).

Furthermore, EUS requires sedation, while ERCP is an invasive technique involving cannulation of the pancreatic and biliary ducts and is highly operator dependent. CT is fairly sensitive for the detection of advanced CP, but less so for early CP. When compared to better tests such as Secretin-CCK function testing, CT is only 47% sensitive in the diagnosis of CP. MRCP is similar to CT for the detection of advanced CP, but not very sensitive to early CP. A benefit of MRCP over CT is improved detection and characterization of biliary and pancreatic strictures, but at a higher cost of about $3,000 per study. S-MRCP uses secretin stimulation and magnetic resonance imaging (MRI) to assess CP. A problem here is that it measures volume of pancreatic flow rather than bicarbonate concentration. In addition, MR images acquired over 30 min, may be insufficient time for secretin stimulation and may lead to reduced sensitivity of the test. Finally, it is an expensive test and has the problems associated with secretin administration. All of the radiologic imaging cited above are highly dependent on the clinician as they need manual visualization and interpretation of anatomic structures.

For a radiological imaging to be capable of detecting early CP, an appropriate molecular probe is needed. For example, as described in U.S. Pat. Nos. 9,155,513, 10,076,299, 11,615,881, and 12,009,090, which are expressly incorporated herein by reference, a patient may be injected with a standard low dose Technetium-99m sulfur colloid radioisotope and scanned with a SPECT scanner. As illustrated in FIGS. 1A and 1B, planar and transverse images, which show the radioisotope in the liver, spleen, and bone marrow, are acquired and processed to determine indices of liver disease, including perfused hepatic mass (PHM), functional liver volume (fLV), functional spleen volume (fSV), and hepatic activity index (HAI). Functional volume, such as the fLV and fSV, may be determined using a "concentration" of radioisotope counts, whereas organ function, such as the PHM and HAI, may be determined from ratios of radioisotope counts, hereinafter, referred to as "ratiometric" methods.

With respect to determining pancreas health, it has been shown that the sensitivity of an MRI may be improved by using a zinc-responsive MRI sensor with low affinity for Zn2+ ions (see André F. Martins, Veronica Clavijo Jordan, Filip Bochner, Sara Chirayil, Namini Paranawithana, Shan-rong Zhang, Su-Tang Lo, Xiaodong Wen, Piyu Zhao, Michal Neeman, and A. Dean Sherry, "*Imaging Insulin Secretion from Mouse Pancreas by MRI Is Improved by Use of a Zinc-Responsive MRI Sensor with Lower Affinity for Zn2+ Ions,*" Journal of the American Chemical Society, 2018, 140, 17456-17464). The MRI showed that "hot spots" can be seen in the pancreatic tail after administration of glucose to stimulate insulin secretion. This detects functional release of Zn2+, but not necessarily Zn2+ content. Also, not all of the mouse pancreas are clearly identifiable in vivo by MRI. Furthermore, respiration makes imaging difficult. To overcome these problems, a surgically sutured "window" was made in the abdomen to help restrict movement of the pancreas tail, something not practical for humans. This technique is in the research phase. It has also been shown that a zinc-chelating imaging probe (ZCIP) labeled with 99mTc radioisotope can be used for imaging the pancreas using single photon emission computerized tomography (SPECT) (see Venkateswararao Eeda, Andria Hedrick, Vibhudutta Awasthi, "*Design of 99mTc-labeled zinc-chelating imaging probe for SPECT imaging of the pancreas,*" Bioorganic & Medicinal Chemistry Letters, 52 (2021) 128385. Mouse SPECT data show the ability of 99mTc-ZCIP to image the pancreas with high sensitivity in a non-invasive manner.

Thus far, a ratiometric technique has not been developed to determine the health of a pancreas. It should be appreciated that the ratiometric techniques described in U.S. Pat. Nos. 9,155,513, 10,076,299, 11,615,881, and 12,009,090 assume that that the liver is the only active organ (i.e., an organ that can provide energy to move the radioisotope against a concentration gradient) that takes up the Technetium-99m sulfur colloid, with the Technetium-99m sulfur colloid not taken up by the liver being taken up passive organs (i.e., organs that can only move the isotope along the concentration gradient), and in this case, the spleen and bone marrow. In contrast, the pancreas is not the only active organ that takes up 99mTc-ZCIP. For example, the liver, spleen, and kidney are active organs that also take up the 99mTc-ZCIP. Thus, the 99mTc-ZCIP probe is not specific to the pancreas, making it difficult to ascertain the functionality of the pancreas using ratiometric techniques. That is, because the multiple active organs that take up the 99mTc-ZCIP compete against each other, the ratio of radioisotope counts in the active organ of interest (in this case, the pancreas) relative to the radioisotope counts taken up by passive organs may be affected by the health of (i.e., the ability to uptake the radioisotope by) the other active organs (in this case, the liver, spleen, and kidney).

There, thus, remains a need to accurately and non-invasively determine the functionality of a pancreas independent of the user.

SUMMARY

In accordance with a first aspect of the present inventions, a diagnostic system for determining a health condition of an organ of a patient that has been administered a radioisotope dose uptaken by the organ (e.g., a pancreas) is provided. The diagnostic system comprises at least one processor configured for receiving image data acquired from the patient when the radioisotope dose is active in the patient, analyzing the received image data to determine a functional organ volume index (e.g., a functional pancreas volume (fPV™) index) and an individual organ function index (e.g., an individual pancreas function (iPF™) index), and staging a health of the organ based on the determined functional organ volume index and the determined individual organ function index, e.g., by selecting one of a plurality of different stages, such as normal and at least one stage of decreased health, e.g., a mild decreased health, a moderate decreased health, and a severe decreased health). The diagnostic system further comprises a user interface device configured for communicating the staged health of the organ to a clinician. In an optional embodiment, the processor(s) is further configured for determining an individual organ reserve index (e.g., a iPR™) index) from the determined functional organ volume index and the determined individual organ function index (e.g., by computing a product of the determined functional organ volume index and the determined individual organ function index), in which case, the user interface may be further configured for communicating the determined individual organ reserve to the clinician.

In one embodiment, the processor(s) may be configured for determining the functional organ volume index by deriving a radioisotope count uptaken by the organ and a concentration of the radioisotope in the organ from the received image data, and computing a product of the derived radioisotope count of the organ and a volume of a voxel of the image data divided by the derived concentration of the radioisotope in the organ. In another embodiment, the processor(s) may be configured for determining the individual organ function index by deriving a radioisotope count uptaken by the organ and a radioisotope count perfused into the organ from the received image data, and computing a quotient of the derived radioisotope count uptaken by the organ over the radioisotope count perfused into the organ. The processor(s) may be configured for generating a differential graph of the determined functional organ volume index and the determined individual organ function index, and for staging the health of the organ based on a location of a coordinate of the determined functional organ volume index and the determined individual organ function index within one of a plurality of regions of the differential graph.

In still another embodiment, over a period of time in which the patient has been administered a series of radioisotope doses, the processor(s) may be further configured for repeating the image data receiving and received image data analyzing steps determine a plurality of functional organ volume indices and plurality of individual organ function indices, generating a differential graph of the determined plurality of functional organ volume indices and the determined plurality of individual organ function indices, determining a trajectory based on locations of coordinates of the determined plurality of functional organ volume indices and the determined plurality of individual organ function indices in the differential graph, and determining a disease prognosis of the patient based on the determined trajectory. In this case, the user interface may be further configured for communicating the determined disease prognosis to the clinician.

In accordance with a second aspect of the present inventions, a diagnostic method of determining a health condition of an organ (e.g., a pancreas) of a patient is provided. The diagnostic method comprises administering a radioisotope dose to the patient, such that the organ uptakes the radioisotope (e.g., Technetium$^{99m}$), acquiring imaging data (e.g., using a functional scanner) from the patient when the radioisotope dose is active in the patient, analyzing the acquired image data to determine a functional organ volume index (e.g., a functional pancreas volume (fPV™) index) and an individual organ function index (e.g., an individual pancreas function (iPF™) index), staging a health of the organ based on the determined functional organ volume index and the determined individual organ function index, and communicating the staged health of the organ to a clinician. The health of the organ may be staged, e.g., by selecting one of a plurality of different stages, such as normal and at least one stage of decreased health, e.g., a mild decreased health, a moderate decreased health, and a severe decreased health). An optional method may further comprise determining an individual organ reserve index (e.g., a iPR™) index) from the determined functional organ volume index and the determined individual organ function index, and communicating the determined individual organ reserve to the clinician. A method of treating the patient may comprise performing the afore-described diagnostic method on a pancreas of the patient having chronic pancreatitis (CP), and treating the CP based on the staged health of the pancreas.

In one method, determining the functional organ volume index comprises deriving a radioisotope count uptaken by the organ and a concentration of the radioisotope in the organ from the acquired image data, and computing a product of the derived radioisotope count of the organ and a volume of a voxel of the image data divided by the derived concentration of the radioisotope in the organ. In another method, determining the individual organ function index may comprise deriving a radioisotope count uptaken by the organ and a radioisotope count perfused into the organ from the acquired image data, and computing a quotient of the derived radioisotope count uptaken by the organ over the radioisotope count perfused into the organ. The diagnostic method may further comprise generating a differential graph of the functional organ volume index and the determined individual organ function index, wherein a health of the organ is staged based on a location of a coordinate of the determined functional organ volume index and the determined individual organ function index within one of a plurality of regions of the differential graph.

Still another method may further comprise repeating the radioisotope administering, image data acquisition, and acquired image data analyzing steps to determine a plurality of functional organ volume indices and plurality of individual organ function indices, generating a differential graph of the determined plurality of functional organ volume indices and the determined plurality of individual organ function indices, determining a trajectory based on locations of coordinates of the determined plurality of functional organ volume indices and the determined plurality of individual organ function indices in the differential graph, determining a organ disease prognosis of the patient based on the determined trajectory, and communicating the determined organ disease prognosis to the clinician.

In accordance with a third aspect of the present inventions, a system of determining a health condition of an active organ (e.g., a pancreas) of a patient that has been administered a radioisotope dose uptaken by the organ and uptaken by at least one other active organ (e.g., a liver, a spleen, and/or a kidney) is provided. The diagnostic system comprises at least one processor configured for receiving image data of the active organ and the other active organ(s) acquired from the patient when the radioisotope dose is active in the patient, deriving a first radioisotope count uptaken by the active organ and at least a second radioisotope count respectively uptaken by the other active organ(s) from the acquired image data, and determining an individual organ function index (e.g., an individual pancreas function (iPF™) index) of the active organ based on the derived first radioisotope count uptaken by the active organ and the derived second radioisotope count(s) uptaken by the other active organ(s), and deriving health condition information of the active organ from the determined individual organ function index. In one embodiment, the derived health condition information may comprise the determined individual organ function index, itself. In another embodiment, the processor(s) is configured for staging a health of the active organ based on the determined individual organ function index, such that the derived health condition information comprises the staged health of the active organ. The diagnostic system further comprises a user interface device configured for communicating the derived health condition information of the active organ to a clinician.

In one embodiment, the processor(s) may be configured for deriving the first radioisotope count from the acquired image data by identifying a first region of interest in the acquired image data corresponding to the active organ, and accumulating a radioisotope count in the first region of interest, and for deriving the second radioisotope count(s) from the acquired image data by identifying at least one second region of interest in the acquired image data respectively corresponding to the other active organ(s), and accumulating at least one other radioisotope count respectively in the second region(s) of interest.

In another embodiment, the processor(s) may be configured for determining the individual organ function index of the active organ by deriving a radioisotope count perfused into the active organ from the derived first radioisotope count uptaken by the active organ and the derived second radioisotope count(s) uptaken by the other active organ(s), and computing a quotient of the derived first radioisotope count uptaken by the active organ over the derived radioisotope count perfused into the active organ.

In this other embodiment, one of the other active organ(s) may be in series downstream from the active organ, in which case, the processor(s) may be configured for deriving the radioisotope count perfused into the active organ by summing the derived first radioisotope count uptaken by the active organ and one of the derived second radioisotope count(s) corresponding to the one other active organ downstream from the active organ.

In this other embodiment, one of the other active organ(s) may be in parallel stream with the active organ, in which case, the processor(s) may be configured for deriving the radioisotope count perfused into the active organ by determining a first functional organ volume index of the active organ and a second functional organ volume index of the one other active organ from the acquired image data, and performing a function of the determined first functional organ volume index and the determined second functional organ volume index. The performed function may comprise computing a sum of the first functional organ volume index and the second functional organ volume index, and computing a quotient of the first functional organ volume index over the computed sum of the first functional organ volume index and the second functional organ volume index. The performed function may further comprise computing the product of a total radioisotope count perfused into the active organ and the one other active organ and the quotient of the first functional organ volume index over the computed sum of the first functional organ volume index and the second functional organ volume index.

In accordance with a fourth aspect of the present inventions, a diagnostic method of determining a health condition of an organ (e.g., a pancreas) of a patient is provided. The diagnostic method comprises administering a radioisotope dose to the patient, such that the organ uptakes the radioisotope, acquiring imaging data from the patient when the radioisotope dose is active in the patient, deriving a first radioisotope count uptaken by the active organ and at least a second radioisotope count respectively uptaken by the at least one other active organ (e.g., a liver, a spleen, and/or a kidney) from the acquired image data, determining an individual organ function index (e.g., an individual pancreas function (iPF™) index) of the active organ based on the derived first radioisotope count uptaken by the active organ and the derived second radioisotope count(s) uptaken by the other active organ(s), deriving health condition information of the active organ from the determined individual organ function index, and communicating the derived health condition information of the active organ to a clinician. In one method, the derived health condition information may comprise the determined individual organ function index, itself. Another method may further comprise staging a health of the active organ based on the determined individual organ function index, such that the derived health condition information comprises the staged health of the active organ. In a method of treating a patient having chronic pancreatitis (CP), the derived health condition information may indicate CP of the pancreas, in which case, the CP of the pancreas may be treated based on the derived health condition information.

In one method, deriving the first radioisotope count from the acquired image data comprising identifying a first region of interest in the acquired image data corresponding to the active organ, and accumulating a radioisotope count in the first region of interest, and deriving the second radioisotope count(s) from the acquired image data may comprise identifying at least one second region of interest in the acquired image data respectively corresponding to the other active organ(s), and accumulating at least one other radioisotope count respectively in the second region of interest(s).

In another method, determining the individual organ function index of the active organ may comprise deriving a radioisotope count perfused into the active organ from the derived first radioisotope count uptaken by the active organ and the derived second radioisotope count(s) uptaken by the other active organ(s), and computing a quotient of the derived first radioisotope count uptaken by the active organ over the derived radioisotope count perfused into the active organ.

In this other method, one of the other active organ(s) may be in series downstream from the active organ, in which case, deriving the radioisotope count perfused into the active organ may comprise summing the derived first radioisotope count uptaken by the active organ and one of the derived second radioisotope count(s) corresponding to the one other active organ downstream from the active organ.

In this other method, one of the other active organ(s) may be in parallel stream with the active organ, in which case, deriving the radioisotope count perfused into the active organ may comprise determining a first functional organ volume index of the active organ and a second functional organ volume index of the one other active organ(s) from the acquired image data, and performing a function of the determined first functional organ volume index and the determined second functional organ volume index. The performed function may comprise computing a sum of the first functional organ volume index and the second functional organ volume index, and computing a quotient of the first functional organ volume index over the computed sum of the first functional organ volume index and the second functional organ volume index. The performed function may further comprise computing the product of a total radioisotope count perfused into the active organ and the one other active organ and the quotient of the first functional organ volume index over the computed sum of the first functional organ volume index and the second functional organ volume index.

In accordance with a fifth aspect of the present inventions, a diagnostic system for determining a health condition of an organ (e.g., a pancreas) of a patient that has been administered a radioisotope dose uptaken by the organ is provided. The diagnostic system comprises at least one processor configured for receiving image data acquired from the patient when the radioisotope dose is active in the patient, analyzing the received image data to determine a functional organ volume index (e.g., a functional pancreas volume (fPV™) index) and an individual organ function index (e.g., an individual pancreas function (iPF™) index), computing a product of the functional organ volume index and an individual organ function index, and deriving an individual organ reserve index (e.g., a iPR™) index) from the product of the functional organ volume index and an individual organ function index. The diagnostic system further comprises a user interface device configured for communicating the individual organ function index to a clinician.

In one embodiment, the processor(s) may be configured for determining the functional organ volume index by deriving a radioisotope count uptaken by the organ and a concentration of the radioisotope in the organ from the received image data, and computing a product of the derived radioisotope count of the organ and a volume of a voxel of the image data divided by the derived concentration of the radioisotope in the organ. In another embodiment, the processor(s) may be configured for determining the individual organ function index by deriving a radioisotope count uptaken by the organ and a radioisotope count perfused into the organ from the received image data, and computing a quotient of the derived radioisotope count uptaken by the organ over the radioisotope count perfused into the organ.

In accordance with a sixth aspect of the present inventions, a diagnostic method of determining a health condition of an organ of a patient is provided. The diagnostic method comprises administering a radioisotope dose to the patient, such that the organ uptakes the radioisotope, acquiring imaging data from the patient when the radioisotope dose is active in the patient, analyzing the acquired image data to determine a functional organ volume index (e.g., a functional pancreas volume (fPV™) index) and an individual organ function index (e.g., an individual pancreas function (iPF™) index), computing a product of the functional organ volume index and an individual organ function index, and deriving an individual organ reserve index (e.g., a iPR™) index) from the product of the functional organ volume index and an individual organ function index, and communicating the individual organ function index to a clinician.

In one method, determining the functional organ volume index may comprise deriving a radioisotope count uptaken by the organ and a concentration of the radioisotope in the organ from the acquired image data, and computing a product of the derived radioisotope count of the organ and a volume of a voxel of the image data divided by the derived concentration of the radioisotope in the organ. In another method, determining the individual organ function index may comprise deriving a radioisotope count uptaken by the organ and a radioisotope count perfused into the organ from the acquired image data, and computing a quotient of the derived radioisotope count uptaken by the organ over the radioisotope count perfused into the organ.

In a method of treating a patient having chronic pancreatitis (CP), the derived individual organ reserve index may indicate CP of the pancreas, in which case, the method may comprise performing the aforementioned diagnostic method, and treating the CP of the pancreas based on the derived individual organ reserve index.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of preferred embodiments of the present invention, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions need not have all the aspects or advantages shown. An aspect or an advantage described in conjunction with a particular embodiment of the disclosed inventions is not necessarily limited to that embodiment and can be practiced in any other embodiments even if not so illustrated. In order to better appreciate how the above-recited and the other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

Figures 1A, 1B:
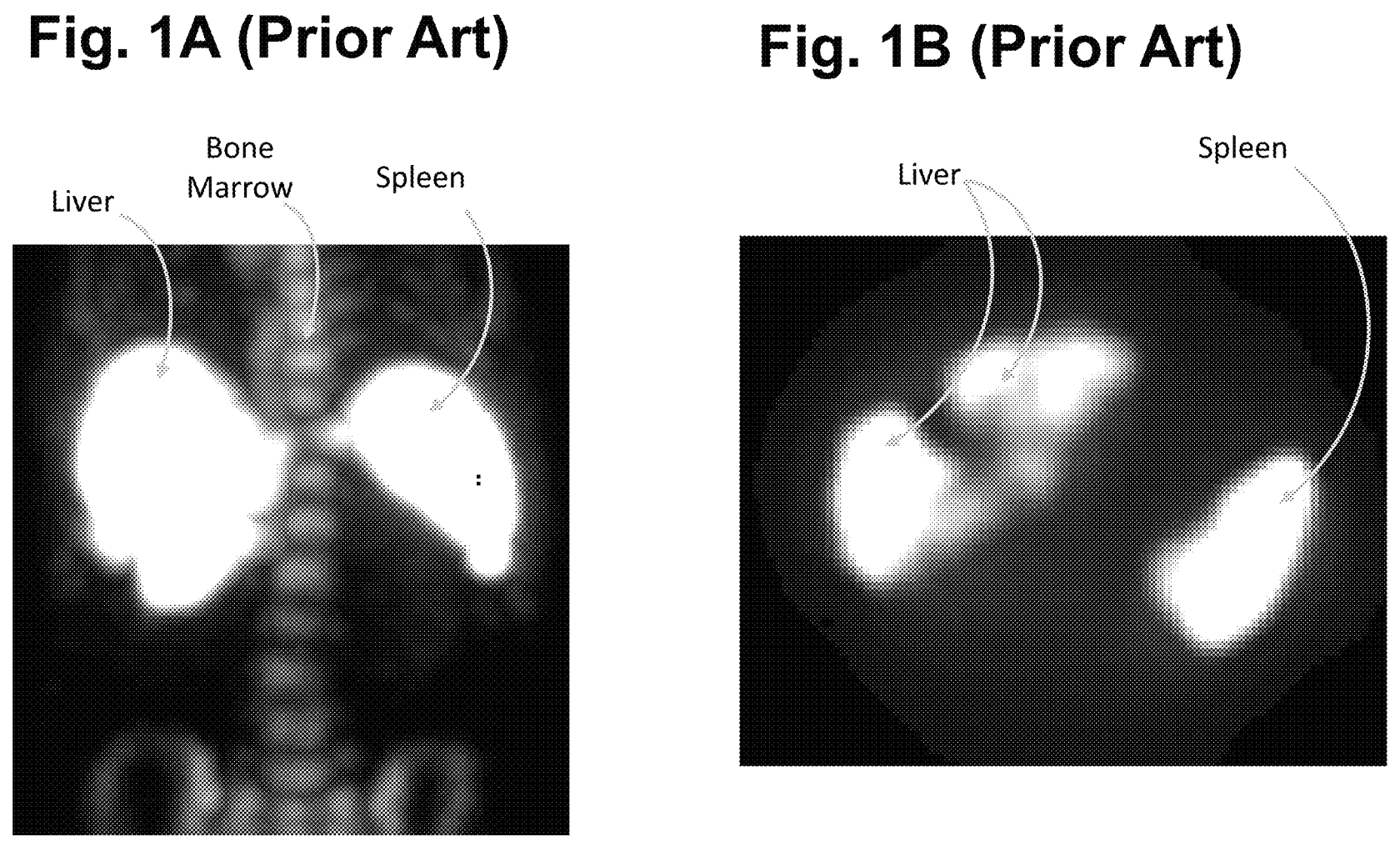

FIGS. 1A-1B are prior art planar and transverse images taken of a liver, bone marrow, and spleen;

FIG. 10 is a timing diagram of an exemplary functional pancreas volume (fPV™) index computed by the diagnostic system of FIG. 2;

FIG. 11 is a timing diagram of an exemplary individual pancreas function (iPF™) index computed by the diagnostic system of FIG. 2;

FIG. 13 is a pictorial diagram of the pancreas, spleen, kidneys, and bladder of a mouse used to perform a study;

US 12,661,076 B2

Figure 2:
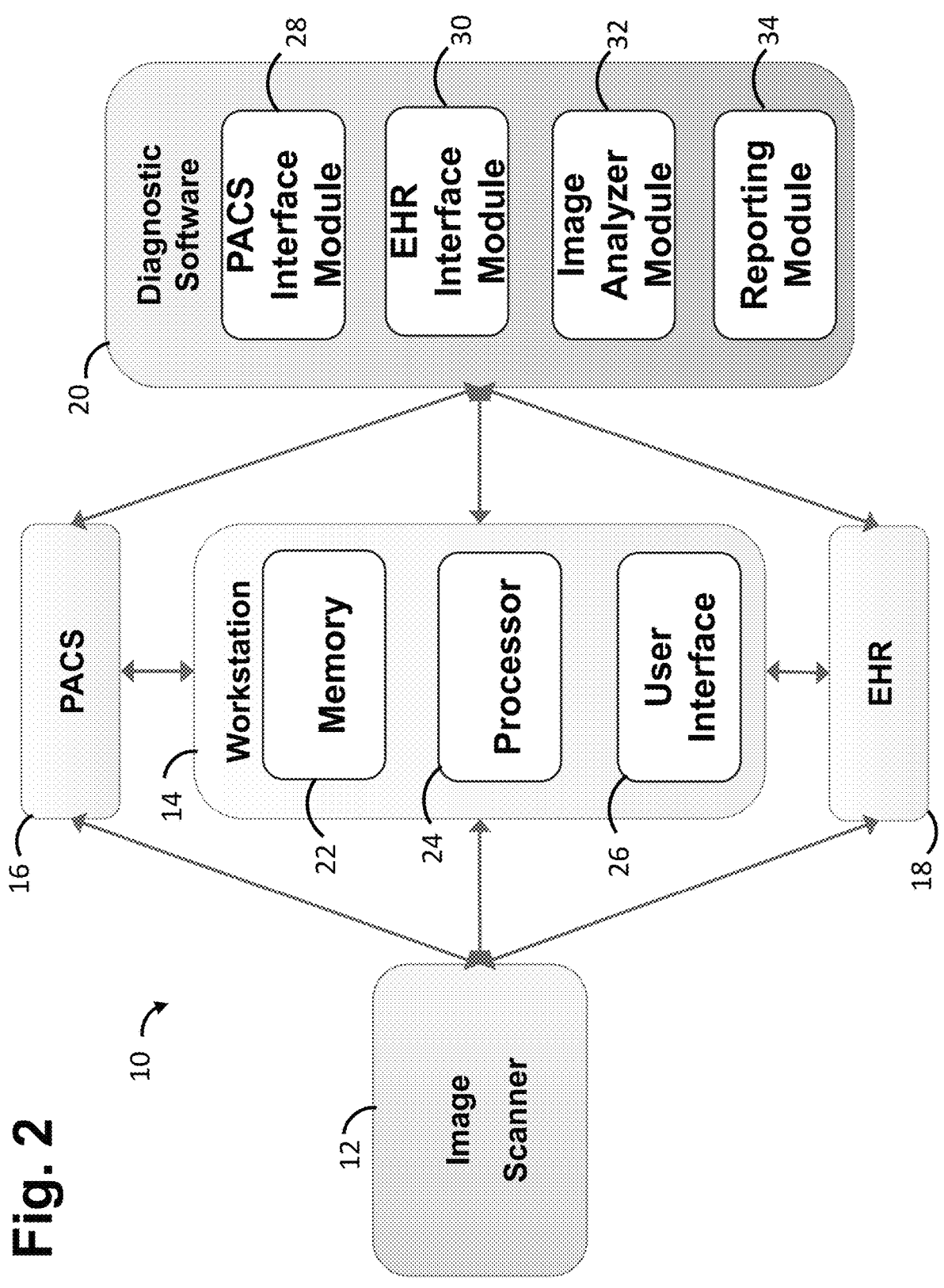
FIG. 2 is a block diagram of one embodiment of a diagnostic system constructed in accordance with the present inventions.
Figure 17:
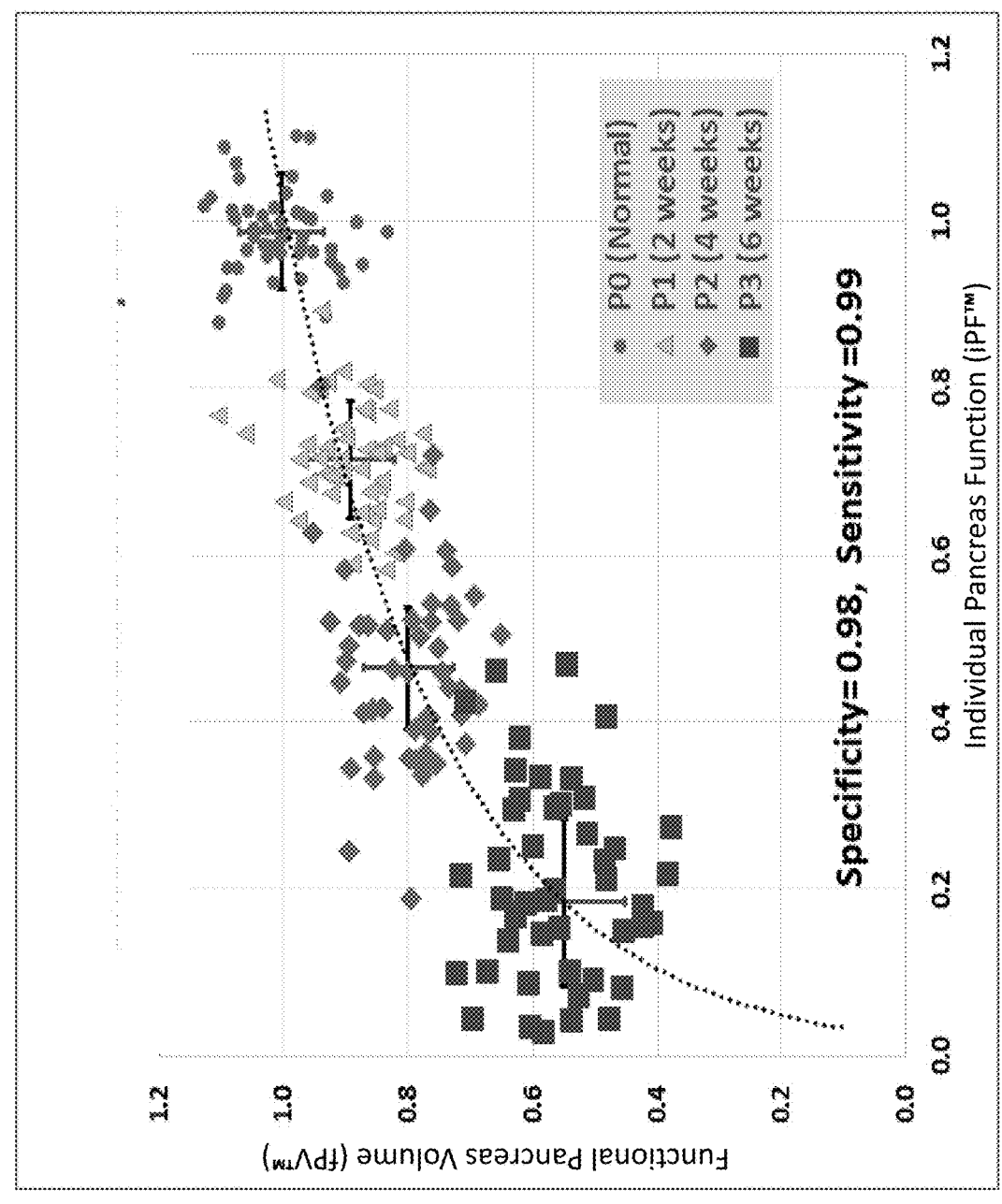
Figure 19:
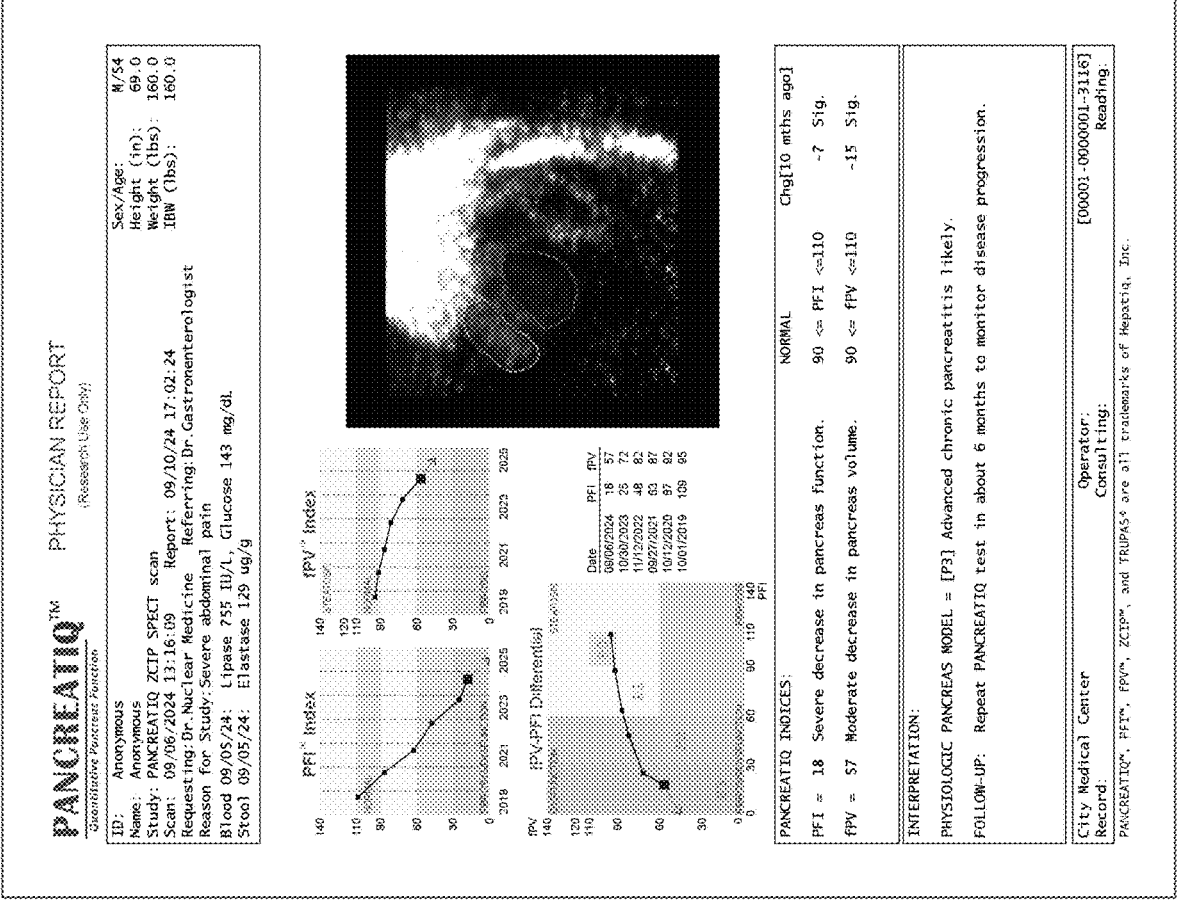

11 ated with the spleen, pancreas, and kidney and accumulated radioisotope counts for the ROIs;

FIG. 15 is a table showing individual pancreas function indices (iPF™) and functional pancreas volume (fPV™) indices computed based on baseline image data and post-cerelein image data acquired from the three mice 2A, 3A, 4A;

Figure 16:
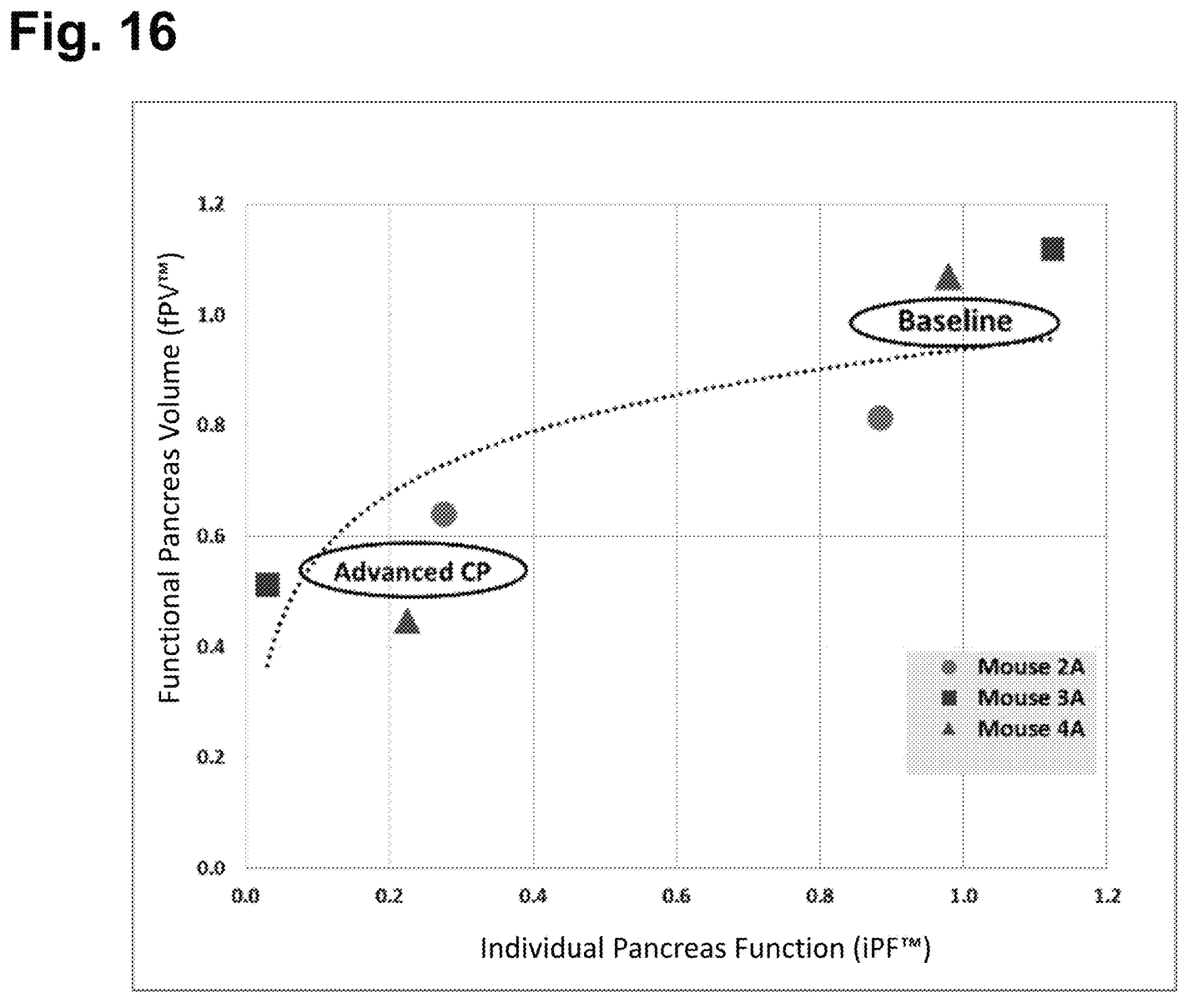

FIG. 16 is a two-dimensional differential graph of three exemplary trajectories of a fPV™ index and a iPF™ index computed from baseline image data and post-cerelein image data acquired from the three mice 2A, 3A, 4A;

FIG. 17 is a two-dimensional differential graph of different stages of the fPV™ indices and iPF™ indices simulated from the baseline image data and post-cerelein image data acquired from the three mice 2A, 3A, 4A;

FIG. 18 is a flow diagram illustrating one method of diagnosing a patient with CP using the diagnostic system 10 of FIG. 2; and FIG. 19 is an exemplary report generated by the diagnostic system 10 of FIG. 2.

DETAILED DESCRIPTION OF THE ILLUSTRATED EMBODIMENTS

Referring now to FIG. 2, one embodiment of a diagnostic system 10 for determining the health condition of an organ (and in this case, the existence and stage of chronic pancreatitis (CP) of a patient) will now be described. The diagnostic system 10 generally comprises an image scanner 12, a workstation 14, a picture and communications system (PACS) 16, an electronic health records (EHR) system 18, and diagnostic software 20.

The image scanner 12 is configured for acquiring image data from the patient that has been administered (injected) with a radioisotope-labeled imaging probe that targets the particular organ to be diagnosed (in this case, the pancreas). In the preferred embodiment, the image scanner 12 may be a single photon emission computerized tomography (SPECT) scanner. It is known that zinc is integral to pancreas health, including digestive enzyme activity, glucagon and insulin secretion. Reduction of zinc activity in the pancreas impairs secretory enzyme activity, glycemic control, and is associated with CP and pancreatic cancer.

In the preferred embodiment, a zinc-chelating imaging probe is administered to the patient. One embodiment of a zinc-chelating imaging probe has a chemical structure $C_{28}H_{39}N_7O_9$ having a molecular weight of is 618 g/mol, classifying it as a small molecule (<900 g/mol). This zinc-chelating imaging probe has diethylene triamine pentaacetic acid (DTPA) at one end and bispicolyl-ethylamine (BPEN) at the other end. The zinc-chelating imaging probe is labeled with a radioisotope, and in particular, Technetium$^{99m}$ to which the DTPA binds. Technetium$^{99m}$ has a 6 hour half-life that emits 140 KeV gamma-rays detectable by a SPECT scanner. With the zinc-chelating imaging probe strongly binding to zinc at one end, and the SPECT scanner detecting the gamma-ray emissions from the Technetium$^{99m}$ at the other end, radiation counts from the detection of the gamma-ray emissions will correlate with the zinc activity in the pancreas, which will decrease due to cellular abnormalities.

Exemplary SPECT and hybrid SPECT/CT scanners are commercially available from several manufacturers, such as General Electric Healthcare. Although the image scanner 12 is preferably a SPECT or hybrid SPECT/CT scanner, it should be understood that the image scanner 12 may alternatively include other types of suitable scanners, e.g., positron emission tomography (PET), PET/CT, functional magnetic resonance imaging (fMRI), or functional CT (fCT) scanners.

The workstation 14 can be any computing device, such as a personal computer, a server, mobile computing devices, scanners, ASICS, or FPGAs. The workstation 14 comprises a memory 22 configured for storing the diagnostic software 20, and a processor (e.g., a central processing unit (CPU)) 22 configured for running the diagnostic software 20 stored in the memory 22. The workstation 14 may also include a user interface 26 that includes an input device (not shown) (e.g., a mouse, keyboard, trackball, touchpad, joystick, touchscreen, etc.) and a display screen (not shown). A preferred embodiment of the workstation 14 is a personal computer running the Windows® operating system, although the workstation 14 may include other types of computing devices, including tablet computers, smart phones, and the image scanner 12, itself. It should also be understood that the workstation 14 may have other types of operating systems, including Apple® and Android® operating systems.

The PACS 16 is configured for storing the image data acquired by the image scanner 12 from the patient. Exemplary PACS's are commercially available from vendors, such as Mckesson Radiology. Although the PACS 16 is a preferred embodiment for an image storage system, it should be understood that other types of image storage systems may be used, including the image scanner 12, itself.

The EHR system 18 is configured for storing patient data, including demographics, clinical indications, medications, laboratory results, genetics, history, etc. Exemplary EHR's are commercially available from vendors, such as EPIC. Although the EHR 16 is a preferred embodiment for a health data storage system, it should be understood that other types of health data storage systems may be used.

The diagnostic software 20 may take the form of executable logic or instructions and/or data or information, which when executed by the processor 24 of the workstation 14 perform the diagnostic functions described below. The diagnostic software 20 may be stored on non-transitory computer-readable media, including but not limited to, random access memory (RAM), read-only memory (ROM), electrically erasable programmable read-only memory (EEPROM), flash memory, compact disc (CD)-ROM, digital versatile disc (DVD), or other optical storage, magnetic cassettes, magnetic tape, magnetic disk storage or other magnetic storage devices, or any other medium which can be used to store the desired information and which can be accessed by a computing device. Alternatively, the diagnostic software may execute on a separate processor (not shown) connected to the workstation by a network or the internet cloud.

The diagnostic software 20 comprises a PACS interface module 28 that transfers image data from the PACS 16 to the workstation 12 and transfers organ (in this case, pancreas) health reports from the workstation 12 to the PACS 16, and an EHR interface module 30 that transfers patient data from the EHR system 18 to the workstation 12 and transfers pancreas health reports from the workstation 12 to the EHR system 18. The diagnostic software 20 further comprises an image analyzer module 32 that analyzes the image data received from the PACS 16, generates various quantitative organ health indices. As will be described in further detail below, such organ health indices include a functional organ volume index (or indices generated over a period of time), an individual organ function index (or indices generated over a period of time), individual organ type index (or indices generated over a period of time), and an individual organ reserve index (or indices generated over a period of time) based on the analysis of the image data and patient data. In this case where the organ is a pancreas, the functional organ volume index, individual organ function index, individual organ type index, and individual organ reserve index may be a functional pancreas volume (fPV™) index, individual pancreas function (iPF™) index, individual pancreas type (iPT™) index, and individual pancreas reserve (iPR™) index.

The diagnostic software 20 further comprises a reporting module 34 that generates the pancreas health report for display on the workstation 12 via the user interface 26 and for transfer to the PACS 16 and EHR system 18 via the respective PACS interface module 28 and EHR interface module 30. The pancreas health report contains health condition information of the pancreas of the patient, including the pancreas health indices, pancreatic disease prognosis, staged function of the pancreas, as well as any patient information received from the EHR system 18. It should be understand that, although the PACS interface module 28, EHR interface module 30, image analyzer module 32, and reporting module 34 are in the preferred embodiment, the diagnostic software 20 may include different modules, additional modules, or fewer modules.

Further details discussing diagnostic systems are disclosed in U.S. Pat. Nos. 9,155,513, 10,076,299, 11,615,881, and 12,009,090, which are expressly incorporated herein by reference.

As briefly discussed above, the diagnostic software 20 is capable of generating various quantitative organ health indices based on an analysis of image data acquired from the patient that has been administered radioisotope-labeled imaging probe. Significantly, these health indices provide an objective measure of the level of disease in an organ, and in this case, the pancreas. Notably, disease processes can lead to fibrosis (or scar tissue formation) in an organ. Portions of the organ affected by fibrosis become non-functional. Those non-functional portions of the organ will, thus, not take up any of the radioisotope whether the organ is active or passive. Measuring the drop in radioisotope uptake for a particular organ permits an estimation of the level of disease in that organ.

As described above, these health indices may include a functional organ volume index, an individual organ function index, an individual organ type index, and an individual organ reserve index. The functional organ volume index (and in the case of a pancreas, the fPV™ index) represents an estimation of the functioning volume of a particular organ (i.e., the number of cells capable of performing the functions of the organ), and thus reflects the extent of fibrosis in the organ. The individual organ function index (and in the case of a pancreas, the iPF™ index) represents an estimation of the percentage of radioisotope that is input into the organ is capable of taking up, and thus reflects both average cell activity (extent of dysfunction) and extent of fibrosis in the organ. The individual organ type index (and in the case of a pancreas, the iPT™ index) is a calibration or standardization factor that takes the characteristics of the patient, including gender, age, height, biomarkers, and genetics. The individual organ reserve index (and in the case of pancreas, the iPR™ index) is a function of the functional organ volume index, the individual organ function index, and the individual organ type index, and provides an indication of the ability of an organ to maintain its functions despite disease or injury, and is crucial for patients undergoing organ surgery or non-surgical treatments for conditions like cancer in the organ.

Given an arbitrary active organ and one or more passive organs downstream from the active organ, the diagnostic software 20 can determine the above-described health indices of that active organ. For example, with reference to FIG. 3, $I_n$ radioisotope counts are input (i.e. perfused) into Active Organ n, $K_n$ radioisotope counts of which are taken up by Active Organ n, and $O_n$ radioisotope counts of which are not taken up by Active Organ n, and thus, output (i.e., perfused) from Active Organ n. Notably, in a typical situation, not all of the circulating radioisotope counts injected into the patient will be taken up by the organs, including Active Organ n, during the initial cardiac cycle. Thus, any of the circulating radioisotope counts not taken up by the organs of the patient during the initial cardiac cycle will be repeatedly recycled through the circulatory system of the patient during subsequent cardiac cycles, preferably until all of the recycled radioisotope counts have been taken up by the organs of the patient, including Active Organ n. It follows that the radioisotope counts $I_n$ input into Active Organ n, the radioisotope counts $K_n$ taken up by Active Organ n, and the radioisotope counts $O_n$ not taken up and output by Active Organ n represent cumulative radioisotope counts that incrementally increase over a multitude of cardiac cycles until steady state has been reached (i.e., all radioisotope counts injected into the patient have been taken up by the organs of the patient).

The $K_n$ radioisotope counts taken up by Active Organ n may be derived from the acquired image data by identifying a region of interest ($ROI_n$) associated with Active Organ n in the acquired image data, and accumulating all of the radiation counts in $ROI_n$. The concentration of radioisotope $C_n$ taken up by Active Organ n may be derived from the acquired image data by taking several samples in $ROI_n$ and combining them. Those skilled in the art would understand that there are many techniques for sampling and many ways of combining samples, ranging from random sampling to a selective sampling of the high concentrations and/or low concentrations in $ROI_n$. These samples collected may be combined using averaging techniques or by fitting a complex frequency distribution to the data. Frequency distribution would depend on the scan parameters and a calibration with a known volume. Further details discussing the identification of regions of interest in imaging data and the derivations of radioisotope counts and radioisotope concentrations from image data are set forth in U.S. Pat. Nos. 9,155,513, 10,076,299, 11,615,881, and 12,009,090, which have been expressly incorporated herein by reference.

The functional volume index $fV_n$ of Active Organ n may be computed in its simplest form as:

$$fV_n = \frac{\eta_n * \Delta V * K_n}{c_n} + \mu_n, \qquad [1]$$

where $K_n$ and $C_n$ are known values determined above, $\Delta V$ is the known voxel volume of the imaging data, and $\eta_n$ and $\mu_n$ are calibration constants for Active Organ n. Those skilled in the art would know that more complex functions may be used for a more accurate calibration. Furthermore, calibration can be implemented as a deep learning neural network that improves over time as more patients are diagnosed and additional data is accumulated on different population groups. In a preferred embodiment, Active Organ n is a pancreas, such that the functional volume index $fV_n$ of Active Organ n set forth in equation [1] may be expressed as the previously mentioned functional pancreas volume (fPV™) index.

It should be appreciated that, given some simplifying assumptions, the physiological function of any Active Organ n is proportional to the number of functioning units (i.e., the functioning volume index $fV_n$ computed in accordance with the equation [1]) and the rate of blood flow through those functional units. In general, the more functioning units Active Organ n has, less blood flow is needed for Active Organ n to be considered healthy. In contrast, the less functioning units Active Organ n has, the more blood flow is needed for Active Organ n to be considered healthy. It should be appreciated that if Active Organ n is functioning well (i.e., is relatively healthy), the radioisotope count $K_n$ taken up by Active Organ n will be relatively large, while the radioisotope count $O_n$ not taken up by Active Organ n will be a relatively small percentage of the radioisotope count $K_n$. In contrast, if Active Organ n is not functioning well (i.e., is relatively unhealthy), the radioisotope count $K_n$ taken up by Active Organ n will be relatively small, while the radioisotope count $O_n$ not taken up by Active Organ n will be a relatively large percentage of the radioisotope count $K_n$.

To this end, the individual function index $F_n$ of Active Organ n may be defined as:

$$F_n = \phi(K_n, O_n), \qquad [2]$$

where $\phi$ is an standardization function determined by validation against a known data set, $K_n$ is a known value determined above, and $O_n$ is an unknown value. The individual function index $F_n$ of Active Organ n may be computed in its simplest form as:

$$F_n = \frac{a_n * K_n}{(K_n + O_n)} + \beta_n, \qquad [3]$$

wherein $\alpha_n$ and $\beta_n$ are standardization constants for Active Organ n. Those skilled in the art would know that more complex functions may be used for a more accurate calibration. Furthermore, calibration can be implemented as a deep learning neural network that improves over time as more patients are diagnosed and additional data is accumulated on different population groups. The unknown radioisotope count $O_n$ not taken up by and output from Active Organ n may be estimated from the radioisotope count $I_n$ input into Active Organ n in accordance with the equation:

$$O_n = I_n - K_n, \qquad [4]$$

where $I_n$ and $K_n$ have been previously defined. As will be described in further detail below, the radioisotope count $I_n$ input into Active Organ n may be estimated from the total amount of radioisotope counts injected into the patient and will depend on the flow relationship of other organs with respect to Active Organ. The total radioisotope counts may be obtained from the image data, i.e., by accumulating all of the radioisotope counts in the image data.

Although a ratiometric technique performed in accordance with equation [3] is preferred to more accurately quantify the function of Active Organ n (i.e., by isolating Active Organ n taking into account only the radioisotope counts $K_n$ taken up by Active Organ n and the radioisotope counts $O_n$ not taken up by Active Organ n), it should be appreciated that other ratiometric techniques may be performed to quantify the function of Organ n. For example, a ratiometric technique that takes into account the radioisotope counts $K_n$ taken up by Active Organ n and the radioisotope counts taken up by one or more of Passive Organs may be performed to quantify the function of Active Organ n. In a preferred embodiment, Active Organ n is a pancreas, such that the individual function index $F_n$ of Active Organ n may be expressed as the previously mentioned individual pancreas function (iPF™) index.

An individual organ type index $\omega_n$ corresponding to Active Organ n is an n-dimensional vector that may be determined by performing a data cluster analysis on young healthy individuals. Those skilled in the art would know that other equivalent methods may be used instead of or together with the cluster analysis. Furthermore, clustering is implemented as a deep learning neural network that improves over time as more patients are diagnosed with the diagnostic system 10 and additional data is accumulated on different population groups. In a preferred embodiment, Active Organ n is a pancreas, such that the individual organ type index $\omega_n$ may be expressed as the previously mentioned individual pancreas type (iPT™) index.

The functional volume index $fV_n$ of Active Organ n, individual function index $F_n$ of Active Organ n, and individual organ type index $\omega_n$ are independent variables that together capture the organ reserve of Active Organ n. The organ reserve of Active Organ n may be defined as:

$$R_n = \psi(fV_n, F_n, \omega_n), \qquad [5]$$

where $\psi$ is a normalization function determined by validation against a known data set, $fV_n$ and $F_n$ can be computed in accordance with equations [1] and [3] above, and $\omega_n$ can be determined as described above. The organ reserve of Active Organ n may be computed in its simplest form as:

$$R_n = \gamma_n * fV_n * F_n * \omega_n + \delta_n, \qquad [6]$$

where $\gamma_n$ and $\delta_n$ are normalization constants for Active Organ n. In alternative embodiments, the organ reserve Rn of Active Organ n may be based on mathematical functions of the functional volume index $fV_n$ and individual function index $F_n$ of Active Organ n other than the function set forth in equation [6]. For example, in alternative embodiments, exponential factors other than one (e.g., fractional exponents or whole exponents, such as 2, 3, etc.) may be associated with one or both of the functional volume index $fV_n$ and individual function index $F_n$. Those skilled in the art would know that more complex functions may be used for a more accurate normalization. Furthermore, normalization can be implemented as a deep learning neural network that improves over time as more patients are diagnosed and additional data is accumulated on different population groups. In a preferred embodiment, Active Organ n is a pancreas, such that the organ reserve index Rn of Active Organ n may be expressed as the previously mentioned individual pancreas reserve (iPR™) index.

Figure 3:
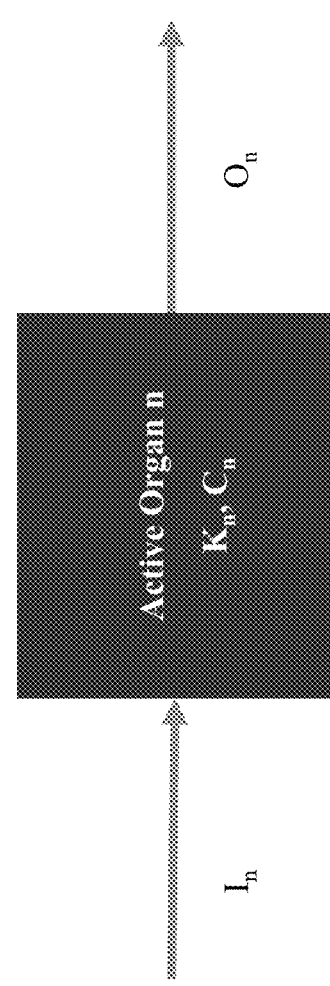
FIG. 3 is a block diagram illustrating a single active organ uptaking a radioisotope.

Although Active Organ n is illustrated in FIG. 3 in isolation, in a typical scenario, Active Organ n will be connected to other organs (whether active or passive) in terms of blood flow. For example, such other organs may be downstream or upstream from Active Organ n, in series with Active Organ n, and/or in parallel with the Active Organ n. Significantly, the diagnostic software 20, and in particular the image analyzer module 32, is capable of generating organ health indices (and in particular, the functional volume index $fV_n$, individual function index $F_n$, individual organ type index $\omega_n$, and organ reserve index Rn) of Active Organ n regardless of the number and configuration of organs (active or passive) that take up the radioisotope.

Figure 4:
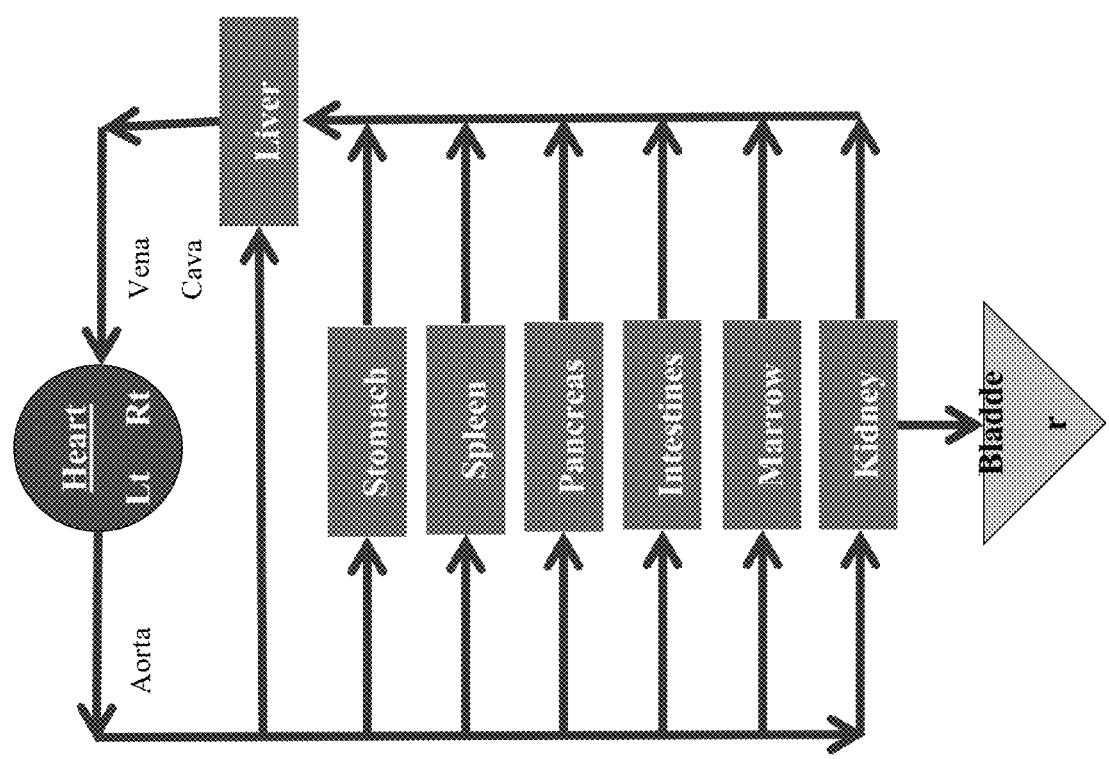
FIG. 4 is a block diagram illustrating a relationship between the major organs in an abdomen with respect to blood flow.

For example, as illustrated in FIG. 4, blood from the heart flows to the major organs in the abdomen (including the liver, stomach, spleen, pancreas, intestines, bone marrow, and kidney) via the aorta and returns from these major organs to the heart via the vena cava. It should be appreciated that FIG. 4 is a simplified illustration as the human body has nearly eighty organs. The liver has two sources of blood supply-one directly from the heart, and the other one indirectly from the heart after passing through the stomach, spleen, pancreas, intestines, bone marrow, and kidneys. The kidneys may filter the blood and dispense urine into the bladder via the ureters (not shown). In terms of blood flow configuration, the liver is in series with, and downstream from, the stomach, spleen, pancreas, intestines, bone marrow, and kidney, while the stomach, spleen, pancreas, intestines, bone marrow, and kidney are in parallel with each other, and upstream and in series with the liver. As described in U.S. Pat. Nos. 9,155,513, 10,076,299, 11,615,881, and 12,009,090, which have been expressly incorporated herein by reference, when a patient is injected with a sulfur-colloid imaging probe labeled with a radioisotope, such as, e.g., Technetium-99m, the liver is the only active organ that takes up the radioisotope, with the spleen and marrow serving as passive organs that provide references for ratiometric computations for the liver. However, when a patient is injected with zinc-chelating imaging probe (ZCIP) labeled with a radioisotope, such as, e.g., Technetium$^{99m}$, the active organs that uptake the radioisotope are the pancreas, liver, spleen, and kidneys. It should be appreciated that bladder serves as a reservoir for radioisotope after being filtered through the kidneys. Thus, the radioisotope count K taken up by the kidneys will be the total radioisotope count accumulated in the ROIs associated with the kidneys, as well as the ROI associated with the bladder.

Figure 5:
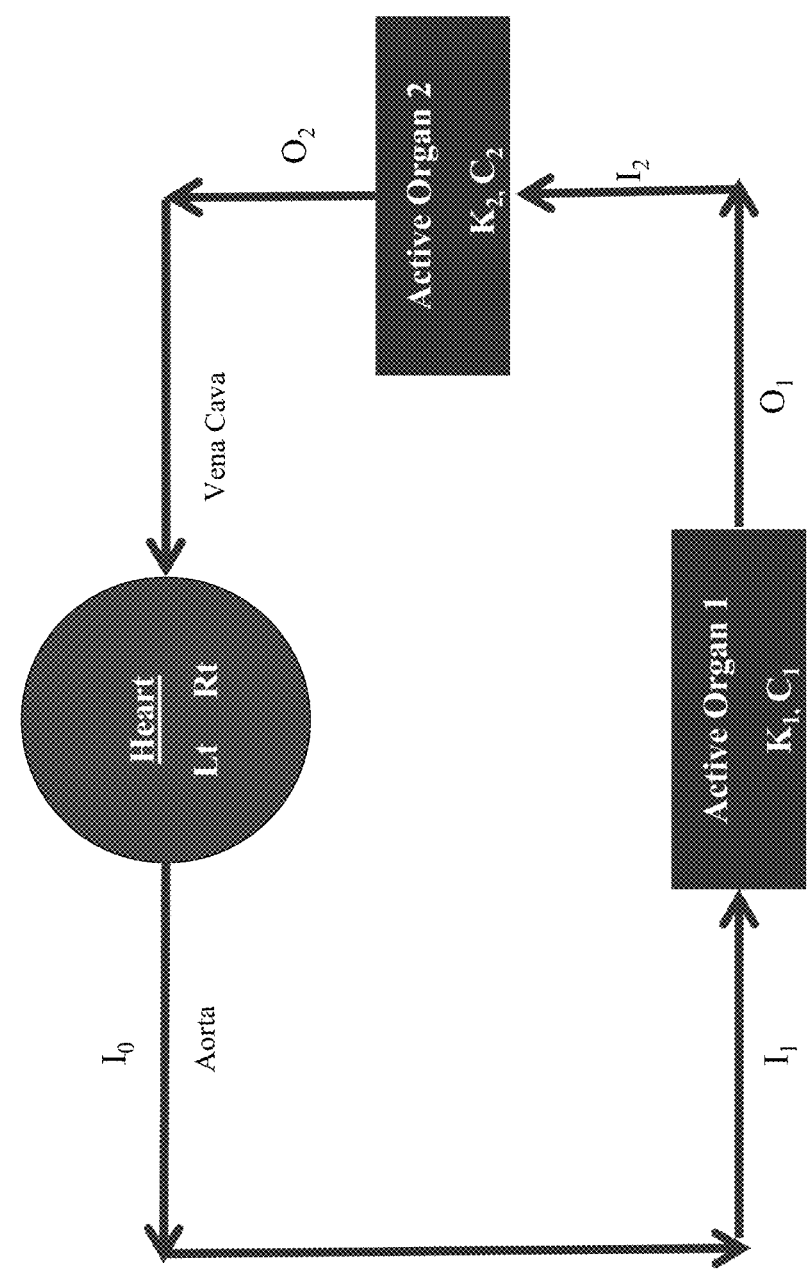
FIG. 5 is a block diagram illustrating a series arrangement of two active organs uptaking a radioisotope.

Given a radioisotope that is predominantly taken up by multiple active organs (Active Organs 1-2) in a serial configuration as illustrated in FIG. 5, the diagnostic software 20 can determine the health indices of each of these organs. In one practical application, Active Organ 1 may be a pancreas, and Active Organ 2 may be a liver, as illustrated in FIG. 4. After injection of the patient with a total of $I_0$ radioisotope counts, $I_n$ radioisotope counts are input into Active Organ 1 from the Heart, $K_1$ radioisotope counts of which are taken up by Active Organ 1, and $O_1$ radioisotope counts of which are not taken up by Active Organ 1, and thus, output from Active Organ 1. $O_1$ radioisotope counts are input into Active Organ 2 as $I_2$ radioisotope counts, $K_2$ radioisotope counts of which are taken up by Active Organ 2, and $O_2$ radioisotope counts of which are not taken up by Active Organ 2, and thus, output from Active Organ 2 back to the Heart.

After the radioisotope counts $K_1$-$K_2$ and concentrations $C_1$-$C_2$ have been obtained from the acquired image data for Active Organs 1-2 by accumulating radioscope counts in and sampling $ROI_1$-$ROI_2$ associated with Active Organs 1-2 in the manner described above, and the total $I_0$ radioisotope counts injected into the patient have been obtained by accumulating the total counts in the imaging data, the functional volume indices $fV_1$, $fV_2$ can be respectively computed for Active Organs 1-2 in accordance with equation [1] above, such that:

$$fV_1 = \frac{\eta_1 * \Delta V * K_1}{c_1} + \mu_1, \qquad [7]$$

where $K_1$ and $C_1$ are known values determined above, $\Delta V$ is the known voxel volume of the imaging data, and $\eta_1$ and $\mu_1$ are calibration constants for Active Organ 1; and $$fV_2 = \frac{\eta_2 * \Delta V * K_2}{c_2} + \mu_2, \qquad [8]$$

known voxel volume of the imaging data, and $\eta_2$ and $\mu_2$ are calibration constants for Active Organ 2.

The individual function indices F1-F2 can be respectively computed for Active Organs 1-2 in accordance with equation [3] above, such that:

$$F_1 = \frac{a_1 * K_1}{(K_1 + O_1)} + \beta_1, \qquad [9]$$

where and $K_1$ is a known value determined above, $\alpha_1$ and $\beta_1$ are standardization constants for Active Organ 1, and $O_1$ is unknown; and $$F_2 = \frac{a_2 * K_2}{(K_2 + O_2)} + \beta_2, \qquad [10]$$

where and $K_2$ is a known value determined above, $\alpha_1$ and $\beta_1$ are standardization constants for Active Organ 2, and $O_2$ is unknown.

The unknown radioisotope counts $O_1$-$O_2$ not taken up and output by Active Organs 1-2 may be estimated as follows. At steady state (when all of the $I_0$ radioisotope counts have been taken up by Active Organs 1-2), and assuming no diversion of any portion of the blood flow from Active Organs 1-2 occurs:

$$I_0 = I_1 = K_1 + K_2 + K_b; \qquad [11]$$

$$O_1 = I_2 = I_1 - K_1; \qquad [12]$$

and $$O_2 = I_2 - K_2, \qquad [13]$$

where $I_0$, $I_1$, $K_1$, and $K_2$ are known values determined above, $O_1$ and $O_2$ are unknown values, and $K_b$ is an unknown background radioisotope count taken up by other organs. The radioisotope count $O_1$ not taken up by, and output from, Active Organ 1 can be obtained by substituting the solution for the radioisotope count $I_1$ in equation [8] into equation [9], such that:

$$O_1 = I_1 - K_1 = K_1 + K_2 + K_b - K_1 = K_2 + K_b. \qquad [14]$$

Similarly, the radioisotope count $O_2$ not taken up by, and output from, Active Organ 2 can be obtained from equations [8] and above. In particular, the solution for the radioisotope count $I_1$ in equations [8]-[9] can be substituted into equation [10], such that:

$$O_2 = I_2 - K_2 = I_1 - K_1 - K_2 = K_1 + K_2 + K_b - K_1 - K_2 = K_b. \qquad [15]$$

The background radioisotope count $K_b$ taken up by other organs can be determined from equation [11], as follows:

$$K_b = I_1 - K_1 - K_2. \qquad [16]$$

For simplicity, the above equations assume that $K_b$ is calculated by imaging the whole body. In practice, if the background counts are relatively small compared to the active and passive organs, they can be estimated from the background counts measured in the portion of the body containing the organs of interest, thus dispensing with the need to scan the whole body.

In the manner that the individual organ index w is determined with respect to the single Active Organ illustrated in FIG. 3, individual organ type indices $\omega_1$-$\omega_2$ corresponding to Active Organs 1-2 can be determined. The organ reserve indices $R_1$-$R_2$ can be respectively computed for Active Organs 1-2 in accordance with equation [6] above, such that:

$$R_1 = \gamma_1 * fV_1 F_1 * \omega_1 + \delta_1, \qquad [17]$$

where $fV_1$ and $F_1$ have been computed in accordance with equations [7] and [9] above, and $\gamma_1$ and $\delta_1$ are normalization constants for Active Organ 1; and $$R_2 = \gamma_2 * fV_2 * F_2 * \omega_2 + \delta_2, \qquad [18]$$

with equations [7] and [9] above, and $\gamma_2$ and $\delta_2$ are normalization constants for Active Organ 2.

Although health indices have been described as being computed for two active organs in the series configuration illustrated in FIG. 5, it should be appreciated that the health indices of more than two active organs in series can be computed.

Figure 6:
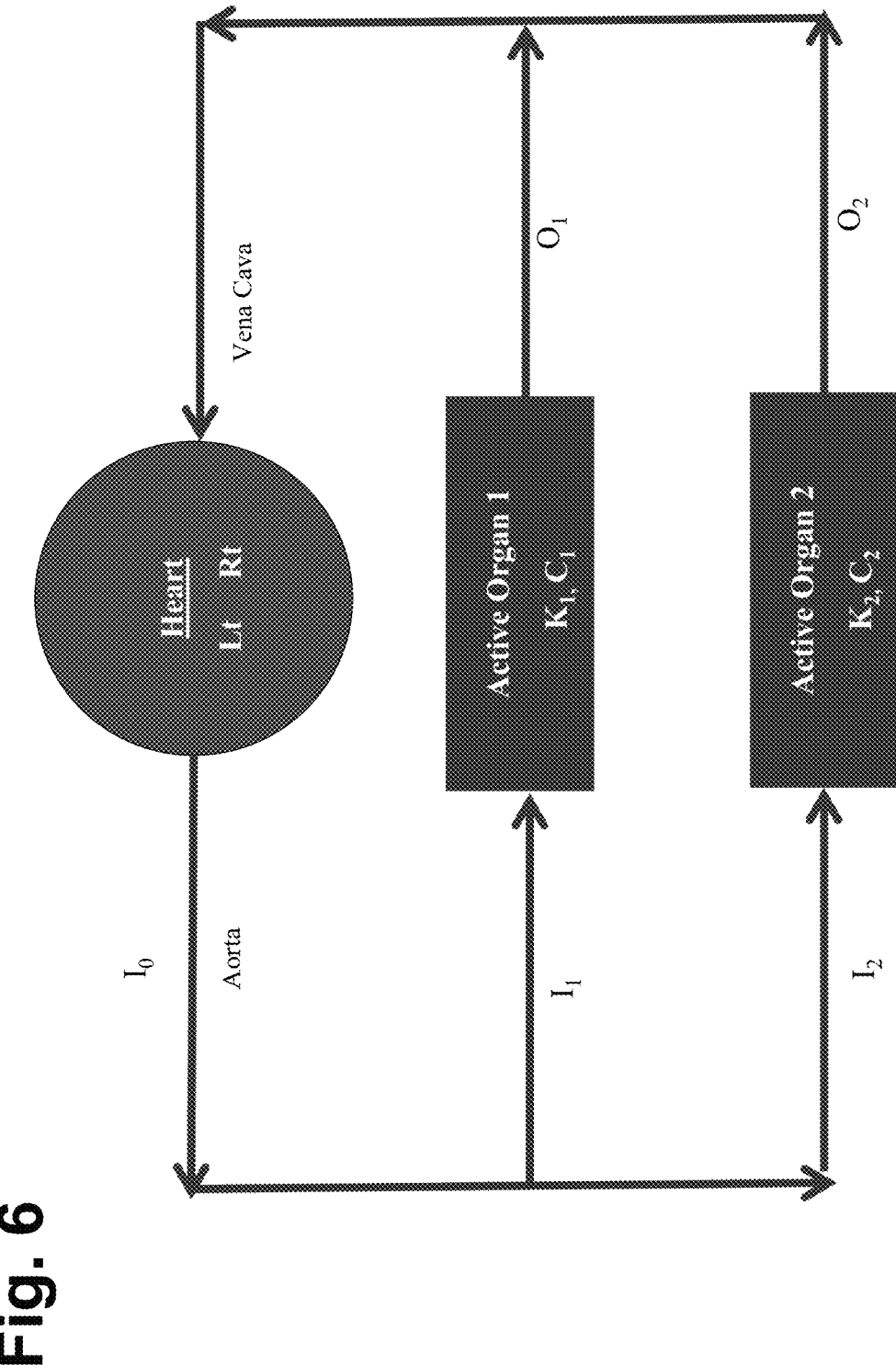
FIG. 6 is a block diagram illustrating a parallel arrangement of two active organs uptaking a radioisotope.

Given a radioisotope that is predominantly taken up by multiple active organs (Active Organs 1-2) in a parallel configuration as illustrated in FIG. 6, the diagnostic software 20 can determine the health indices of each of these organs. In one practical application, Active Organ 1 may be a pancreas, and Active Organ 2 may be a spleen, as illustrated in FIG. 4. After injection of the patient with a total of $I_0$ radioisotope counts, the $I_0$ radioisotope counts are distributed from the Heart as $I_1$-$I_2$ radioisotope counts that are respectively input into Active Organs 1-2. $K_1$ of the radioisotope counts $I_1$ are taken up by Active Organ 1, and $O_1$ of the $I_1$ radioisotope counts are not taken up by Active Organ

1, and thus, output from Active Organ 1 to the Heart. Similarly, $K_2$ of the radioisotope counts $I_2$ are taken up by Active Organ 2, and $O_2$ of the $I_2$ radioisotope counts are not taken up by Active Organ 2, and thus, output from Active Organ 2 to the Heart.

After the radioisotope counts $K_1$-$K_2$ and concentrations $C_1$-$C_2$ have been obtained from the acquired image data for Active Organs 1-2 by accumulating radioscope counts in and sampling $ROI_1$-$ROI_2$ associated with Active Organs 1-2 in the manner described above, and the total $I_0$ radioisotope counts injected into the patient have been obtained by accumulating the total counts in the imaging data, the functional volume indices $fV_1$-$fV_2$ can be respectively computed for Active Organs 1-2 in accordance equations [7] and [8] above, while the individual function indices $F_1$-$F_2$ can be respectively computed for Active Organs 1-2 in accordance with equations [9]-[10] above. For simplicity, the above equations ignore the background radioisotope counts $K_b$, assuming they are relatively small compared to the active and passive organs. In practice, a correction is made for $K_b$, which can be directly measured by imaging the whole body. $K_b$ can also be estimated from the background counts measured in the portion of the body containing the organs of interest, thus dispensing with the need to scan the whole body.

With respect to computing the individual function indices $F_1$-$F_2$ for Active Organs 1-2 in accordance equations [9] and [10], the unknown radioisotope counts $O_1$-$O_2$ not taken up and output by Active Organs 1-2 may be estimated as follows. The inventor has appreciated that the $I_0$ radioisotope counts injected into the patient divides between the radioisotope counts $I_1$ and $I_2$ based on the effective flow resistance of Active Organs 1-2. The greater the flow resistance of an organ the lower the blood flow into that organ. The functional volume indices $fV_1$-$fV_2$ of Active Organs 1-2 can be used to determine the inverse of the flow resistance of Active Organs 1-2. It follows that the greater the functional volume index $fV_1$ of Active Organ 1, the lower the flow resistance of Active Organ 1, and the greater the functional volume index $fV_2$ of Active Organ 2, the lower the flow resistance of Active Organ 2. Thus, assuming that all of the $I_0$ radioisotope counts injected into the patient are distributed as radioisotope counts $I_1$-$I_2$, if:

$$fV_0 = fV_1 + fV_2, \qquad [19]$$

where $fV_0$ is the total functional volume index of Active Organs 1-2, $fV_1$ can be computed in accordance with equation [7], and $fV_2$ can be computed in accordance with equation [8], then:

$$I_1 = I_0 * fV_1 / fV_0; \text{ and}$$

$$I_2 = I_0 * fV_2 / fV_0,$$

where $I_0$, $fV_1$, and $fV_2$ are known values determined above.

The unknown radioisotope counts $O_1$-$O_2$ not taken up and output by Active Organs 1-2 may then be computed by incorporating the values of the radioisotope counts $I_1$-$I_2$ input into Active Organs 1-2 into equations [12]-[13], and the individual function indices $F_1$-$F_2$ of Active Organs 1-2 may then be computed by incorporating the values of radioisotope counts $O_1$-$O_2$ into equations [9]-[10]. The individual organ type indices $\omega_1$-$\omega_2$ corresponding to Active Organs 1-2 can be determined as described above, while the organ reserve indices $R_1$-$R_2$ can be respectively computed for Active Organs 1-2 in accordance with equations [17]-[18] above.

Figure 7:
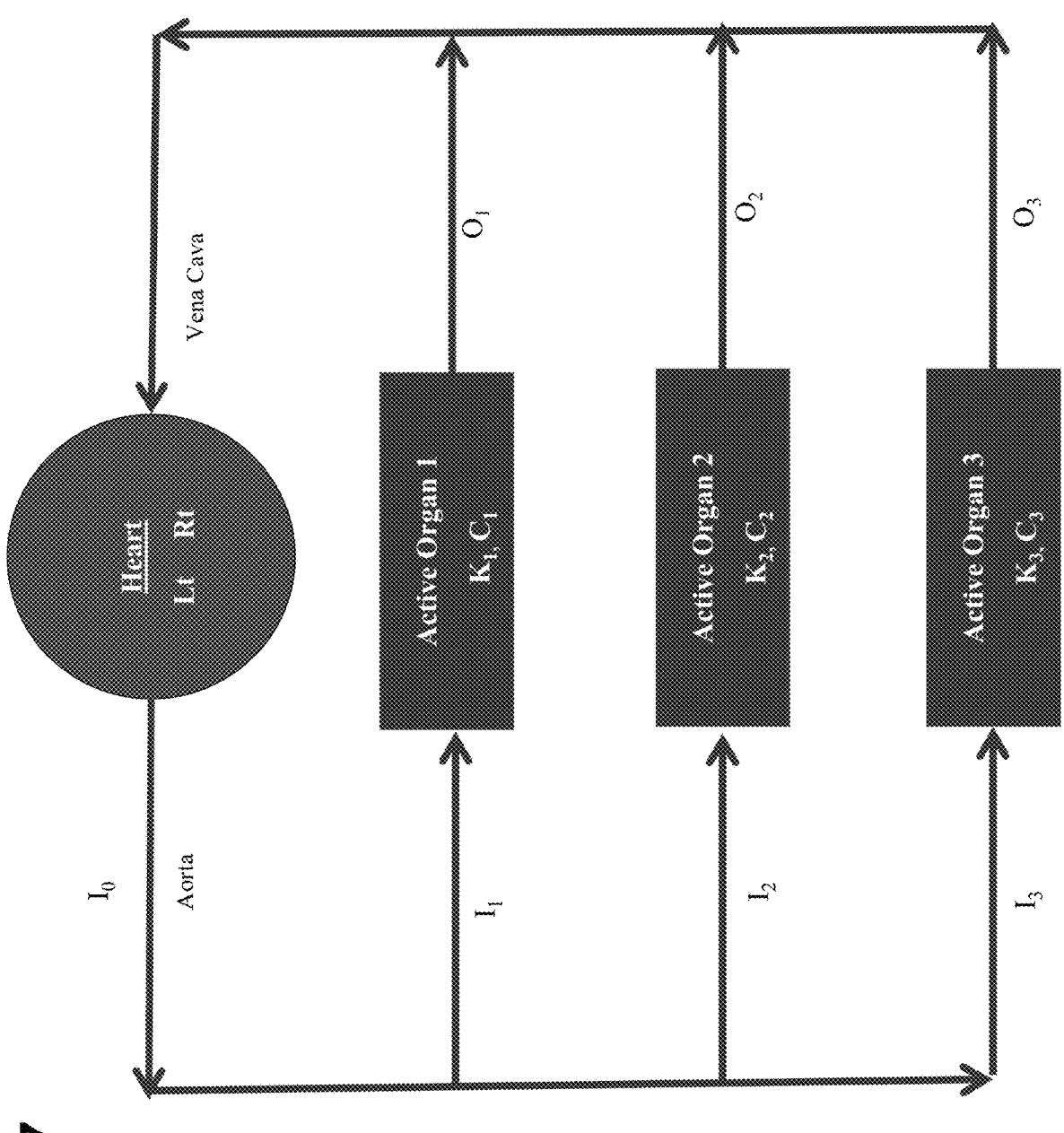
FIG. 7 is a block diagram illustrating a parallel arrangement of three active organs uptaking a radioisotope.

Although health indices have been described as being computed for two active organs in the parallel configuration illustrated in FIG. 6, it should be appreciated that the diagnostic software 20 can determine the health indices of each of an arbitrary number of organs in parallel. For example, as illustrated in FIG. 7, three organs (Active Organ 1, Active Organ 2, and Active Organ 3) are in a parallel configuration. In one practical application, Active Organ 1 may be a pancreas, Active Organ 2 may be a spleen, and Active Organ 3 may be a kidney, as illustrated in FIG. 4.

After injection of the patient with a total of $I_0$ radioisotope counts, the $I_0$ radioisotope counts are distributed from the Heart as $I_1$-$I_3$ radioisotope counts that are respectively input into Active Organs 1-3. $K_1$ of the radioisotope counts $I_1$ are taken up by Active Organ 1, and $O_1$ of the $I_1$ radioisotope counts are not taken up by Active Organ 1, and thus, output from Active Organ 1 to the Heart. Similarly, $K_2$ of the radioisotope counts $I_2$ are taken up by Active Organ 2, and $O_2$ of the $I_2$ radioisotope counts are not taken up by Active Organ 2, and thus, output from Active Organ 2 to the Heart. Similarly, $K_3$ of the radioisotope counts Is are taken up by Active Organ 3, and $O_3$ of the Is radioisotope counts are not taken up by Active Organ 3, and thus, output from Active Organ 3 to the Heart.

After the radioisotope counts $K_1$-$K_3$ and concentrations $C_1$-$C_3$ have been obtained from the acquired image data for Active Organs 1-3 by accumulating radioscope counts in and sampling in $ROI_1$-$ROI_3$ associated with Active Organs 1-3 in the manner described above, and the total $I_0$ radioisotope counts injected into the patient have been obtained by accumulating the total counts in the imaging data, the functional volume indices $fV_1$-$fV_2$ can be respectively computed for Active Organs 1-2 in accordance equations [7]-[8] above, while the individual function indices $F_1$-$F_2$ can be respectively computed for Active Organs 1-2 in accordance with equations [9]-[10] above.

The functional volume index $fV_3$ can be computed for Active Organ 3 in accordance with equation [1] above, such that:

$$fV_3 = \frac{\eta_3 * \Delta V * K_3}{c_3} + \mu_3, \qquad [23]$$

where $K_3$ and $C_3$ are known values determined above, $\Delta V$ is the known voxel volume of the imaging data, and $\eta_3$ and us are standardization constants for Active Organ 3.

The individual function index $F_3$ can be computed for Active Organ 3 in accordance with equation [3] above, such that:

$$F_3 = \frac{a_3 * K_3}{(K_3 + O_3)} + \beta_3, \qquad [24]$$

where and $K_3$ is a known value determined above, $\alpha_3$ and $\beta_3$ are standardization constants for Active Organ 3, and $O_3$ is unknown.

Based on the previously described premise that the $I_0$ radioisotope counts injected into the patient divides between the radioisotope counts $I_1$-$I_3$ based on the effective flow resistance of Active Organs 1-3, and assuming that all of the $I_0$ radioisotope counts injected into the patient are distributed as radioisotope counts $I_1$-$I_3$, if:

$$fV_0 = fV_1 + fV_2 + fV_3, \qquad [25]$$

where $fV_0$ is the total functional volume index of Active Organs 1-3, $fV_1$ can be computed in accordance with equation [7] above, $fV_2$ can be computed in accordance with equation [8] above, and $fV_3$ can be computed in accordance with equation above, then:

$$I_1 = I_0 * fV_1 / fV_0;$$

$$I_2 = I_0 * fV_2 / fV_0; \text{ and}$$

$$I_3 = I_0 * fV_3 / fV_0,$$

where $I_0$ and $fV_1$-$fV_3$ are known values determined above.

The unknown radioisotope counts $O_1$-$O_2$ not taken up and output by Active Organs 1-2 may then be computed by incorporating the values of the radioisotope counts $I_1$-$I_2$ input into Active Organs 1-2 into equations [12]-[13]. The unknown radioisotope count $O_3$ not taken up and output by Active Organ 3 may be computed by incorporating the value of the radioisotope count Is input into Active Organ 3 into:

$$O_3 = I_3 - K_3, \qquad [29]$$

where $I_3$ and $K_3$ are known values determined above. The individual function indices $F_1$-$F_3$ of Active Organs 1-3 may then be computed by incorporating the values of radioisotope counts $O_1$-$O_3$ into equations [9]-[10] and [24].

The individual organ type indices $\omega_1$-$\omega_3$ respectively corresponding to Active Organs 1-3 can be determined as described above, while the organ reserve indices $R_1$-$R_2$ can be respectively computed for Active Organs 1-2 in accordance with equations [17]-[18]. The organ reserve index $R_3$ may be computed for Active Organ 3 in accordance with:

$$R_3 = \gamma_3 * fV_3 * F_3 * \omega_3 + \delta_3, \qquad [30]$$

where $fV_3$ and $F_3$ have been computed in accordance with equations [23]-[24] above, and $\gamma_3$ and $\delta_3$ are normalization constants for Active Organ 3.

Figure 8A:
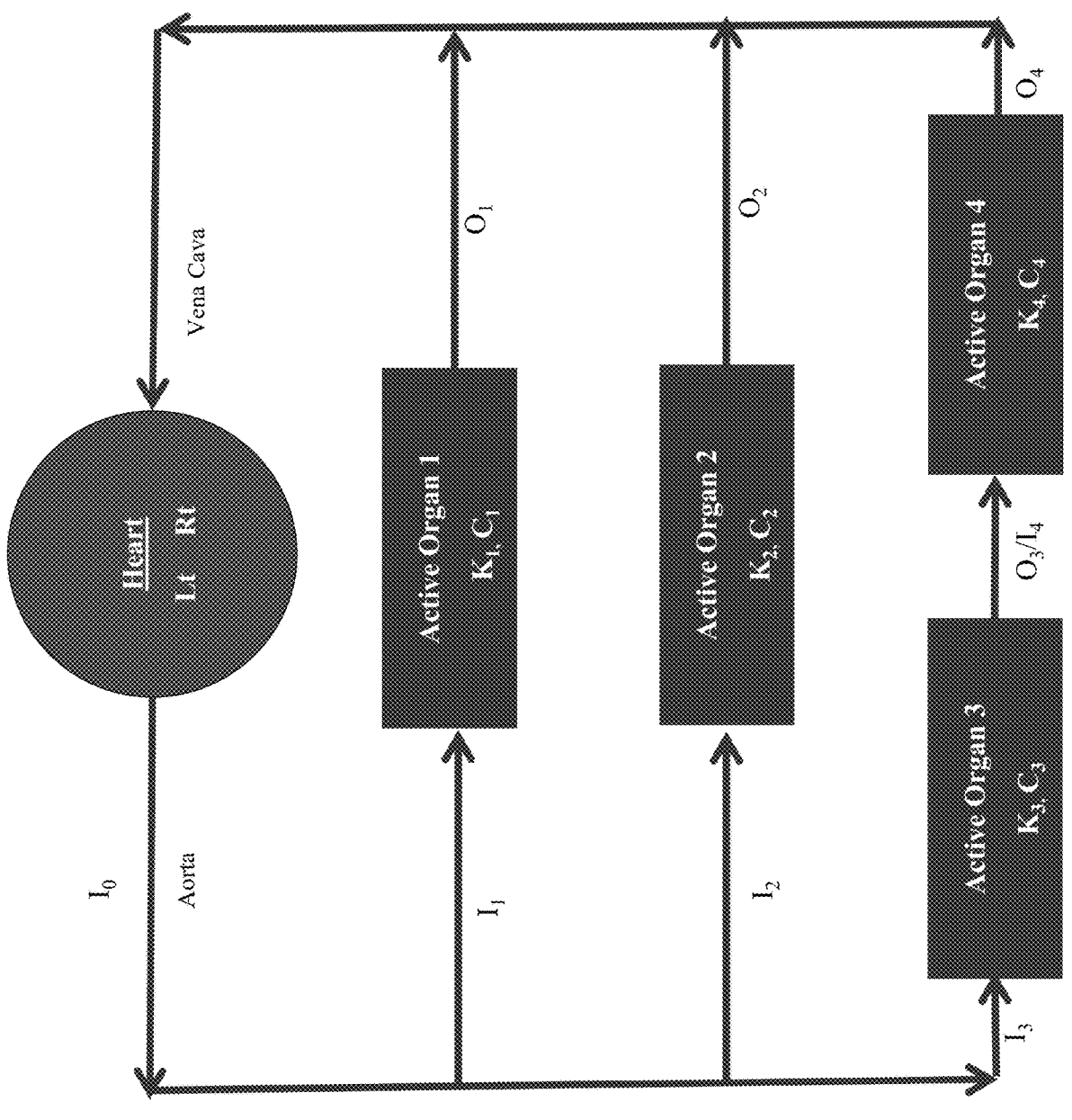
FIG. 8A is a block diagram illustrating a hybrid arrangement of four active organs uptaking a radioisotope.

Given a radioisotope that is predominantly taken up by multiple active organs (Active Organs 1-4) in a hybrid configuration (both a parallel configuration and a serial configuration), as illustrated in FIG. 8A, the diagnostic software 20 can determine the health indices of each of these organs. In one practical application, Active Organ 1 may be a pancreas, Active Organ 2 may be a spleen, Active Organ 3 may be a kidney, as illustrated in FIG. 4. Active Organ 4 may be an arbitrary organ in series with Active Organ 3.

After injection of the patient with a total of $I_0$ radioisotope counts, the $I_0$ radioisotope counts are distributed from the Heart as $I_1$-$I_3$ radioisotope counts that are respectively input into Active Organs 1-3. $K_1$ of the radioisotope counts $I_1$ are taken up by Active Organ 1, and $O_1$ of the $I_1$ radioisotope counts are not taken up by Active Organ 1, and thus, output from Active Organ 1 to the Heart. Similarly, $K_2$ of the radioisotope counts $I_2$ are taken up by Active Organ 2, and $O_2$ of the $I_2$ radioisotope counts are not taken up by Active Organ 2, and thus, output from Active Organ 2 to the Heart. Similarly, $K_3$ of the radioisotope counts Is are taken up by Active Organ 3, and $O_3$ of the Is radioisotope counts are not taken up by Active Organ 3, and thus, output from Active Organ 3 to Active Organ 4. $O_3$ radioisotope counts are input into Active Organ 4 as $I_4$ radioisotope counts, $K_4$ radioisotope counts of which are taken up by Active Organ 4, and $O_4$ radioisotope counts of which are not taken up by Active Organ 4, and thus, output from Active Organ 4 back to the Heart.

After the radioisotope counts $K_1$-$K_4$ and concentrations $C_1$-$C_4$ have been obtained from the acquired image data for Active Organs 1-4 by accumulating radioscope counts in and sampling $ROI_1$-$ROI_4$ associated with Active Organs 1-4 in the manner described above, and the total $I_0$ radioisotope counts injected into the patient have been obtained by accumulating the total counts in the imaging data, the functional volume indices $fV_1$-$fV_3$ can be respectively computed for Active Organs 1-3 in accordance equations [7], [8], and [24] above, while the individual function indices $F_1$-$F_3$ can be respectively computed for Active Organs 1-3 in accordance with equations [9], [10], and [24] above.

The functional volume index $fV_4$ can be computed for Active Organ 4 in accordance with equation [1] above, such that:

$$fV_4 = \frac{\eta_4 * \Delta V * K_4}{c_4} + \mu_4, \qquad [31]$$

where $K_4$ and $C_4$ are known values determined above, $\Delta V$ is the known voxel volume of the imaging data, and $\eta_4$ and $\mu_4$ are calibration constants for Active Organ 3.

The individual function index $F_4$ can be computed for Active Organ 4 in accordance with equation [3] above, such that:

$$F_4 = \frac{a_4 * K_4}{(K_4 + O_4)} + \beta_4, \qquad [32]$$

where and $K_4$ is a known value determined above, $\alpha_4$ and $\beta_4$ is standardization constants for Active Organ 4, and $O_4$ is unknown.

Figure 8B:
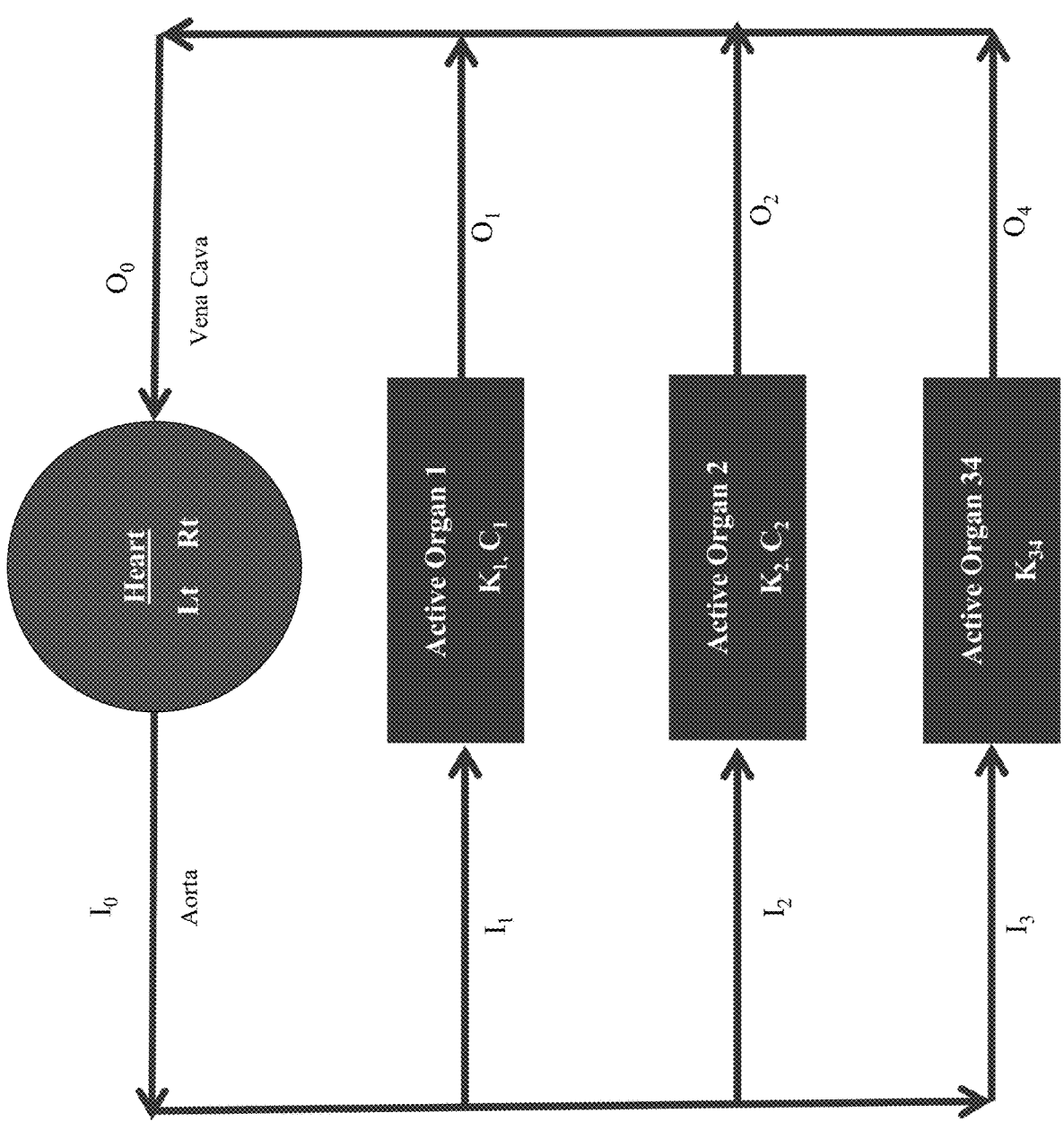
FIG. 8B is a block diagram illustrating a reduced version of the hybrid arrangement of the four active organs of FIG. 8A.

For purposes of determining the radioisotope counts $I_1$-$I_3$, Active Organs 3-4 can be replaced with a single representative Active Organ 34, as illustrated in FIG. 8B. A combined functional volume index $fV_{34}$ of Active Organ 34 may then be computed by summing the previously computed functional volume indices $fV_3$-$fV_4$ of Active Organs 3-4. Based on the previously described premise that the $I_0$ radioisotope counts injected into the patient divides between the radioisotope counts $I_1$-$I_3$ based on the effective flow resistance of Active Organs 1, 2, and 34, and assuming that all of the $I_0$ radioisotope counts injected into the patient are distributed as radioisotope counts $I_1$-$I_3$, if:

$$fV_0 = fV_1 + fV_2 + fV_{34}, \qquad [33]$$

where $fV_0$ is the total functional volume index of Active Organs 1, 2, and 34, $fV_1$ can be computed in accordance with equation [7] above, $fV_2$ can be computed in accordance with equation [8] above, and $fV_{34}$ is the sum of the functional volume indices $fV_3$-$fV_4$ previously computed in accordance with equations and [31], then:

$$I_1 = I_0 * fV_1/fV_0; \qquad [34]$$

$$I_2 = I_0 * fV_2/fV_0; \text{ and} \qquad [35]$$

$$I_3 = I_0 * fV_{34}/fV_0, \qquad [36]$$

where $I_0$, $fV_1$, $fV_2$, and $fV_{34}$ are known values determined above. The unknown radioisotope counts $O_1$-$O_3$ not taken up and output by Active Organs 1-3 may then be computed by incorporating the values of the radioisotope counts $I_1$-$I_3$ input into Active Organs 1-3 into equations [12]-[13], and [29]. The unknown radioisotope count $O_4$ not taken up and output by Active Organ 4 may be computed by incorporating the value of the radioisotope count $I_4$ input into Active Organ 4 into:

$$O_4 = I_4 - K_4, \qquad [37]$$

where $I_4$ is equal to $O_3$, and $K_3$ is a known values determined above. The individual function indices $F_1$-$F_4$ of Active Organs 1-4 may then be computed by incorporating the values of radioisotope counts $O_1$-$O_4$ into equations [9]-[10], [24], and [32].

The individual organ type indices $\omega_1$-$\omega_4$ respectively corresponding to Active Organs 1-4 can be determined as described above, while the organ reserve indices $R_1$-$R_3$ can be respectively computed for Active Organs 1-3 in accordance with equations [17]-[18] and [30] above. The organ reserve index $R_4$ may be computed for Active Organ 4 in accordance with:

$$R_4 = \gamma_4 * fV_4 * F_4 * \omega_4 + \delta_4, \qquad [38]$$

where $fV_4$ and $F_4$ have been computed in accordance with equations [31]-[22] above, and $\gamma_4$ and $\beta_4$ are normalization constants for Active Organ 4.

Figure 9:
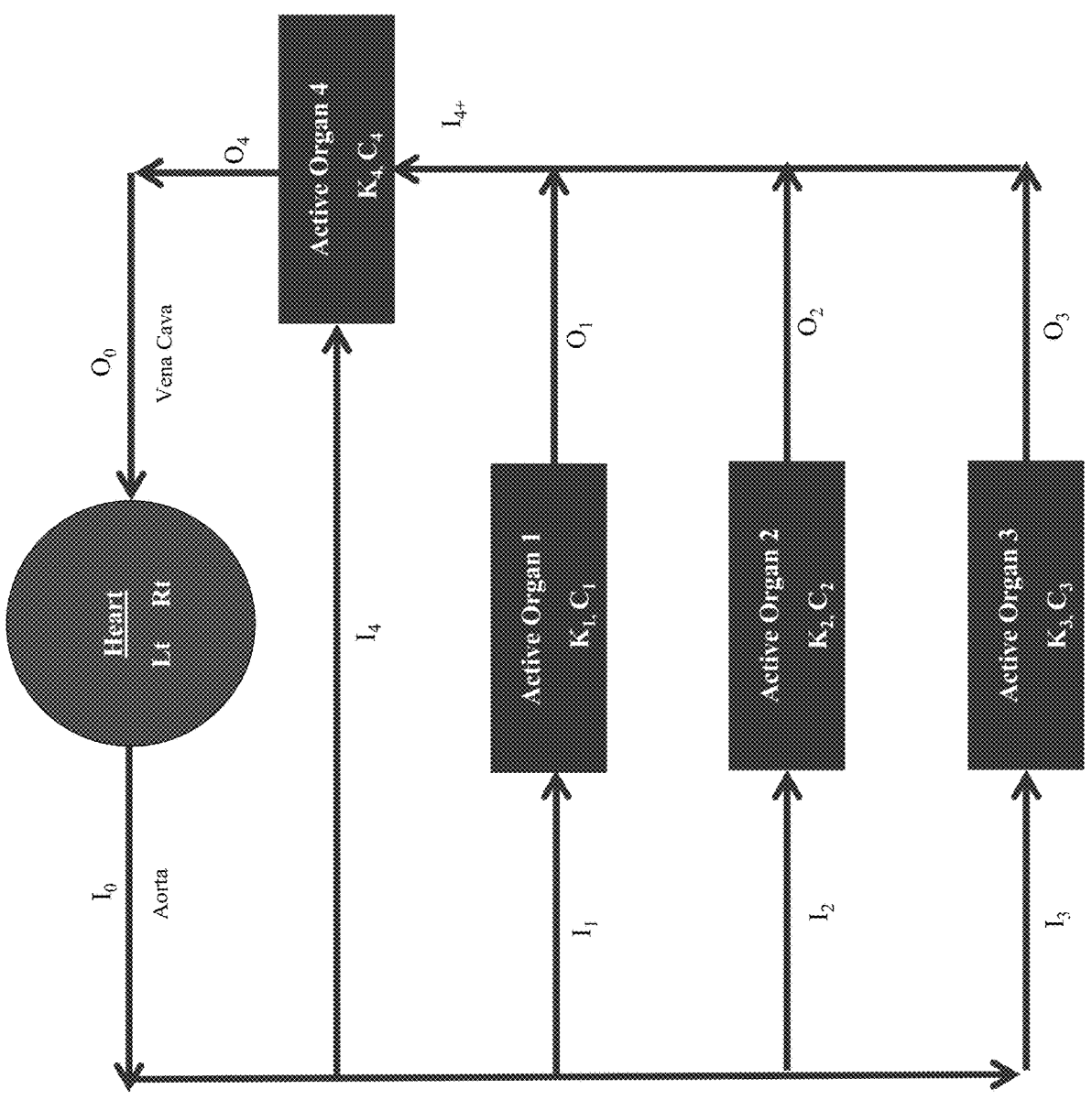
FIG. 9 is a block diagram illustrating another hybrid arrangement of four active organs uptaking a radioisotope.

Given a radioisotope that is predominantly taken up by multiple active organs (Active Organs 1-4) in a hybrid configuration (both a parallel configuration and a serial configuration), as illustrated in FIG. 9, the diagnostic software 20 can determine the health indices of each of these organs. In one practical application, Active Organ 1 may be a pancreas, Active Organ 2 may be a spleen, Active Organ 3 may be a kidney, and Active Organ 4 may be a liver, as illustrated in FIG. 4. In this case, the Active Organ 4 is both in parallel with Active Organs 1-3 and in series with Active Organs 1-3.

After injection of the patient with a total of $I_0$ radioisotope counts, the $I_0$ radioisotope counts are distributed from the Heart as $I_1$-$I_4$ radioisotope counts that are respectively input into Active Organs 1-4. $K_1$ of the radioisotope counts $I_1$ are taken up by Active Organ 1, and $O_1$ of the $I_1$ radioisotope counts are not taken up by Active Organ 1, and thus, output from Active Organ 1. Similarly, $K_2$ of the radioisotope counts $I_2$ are taken up by Active Organ 2, and $O_2$ of the $I_2$ radioisotope counts are not taken up by Active Organ 2, and thus, output from Active Organ 2. Similarly, $K_2$ of the radioisotope counts Is are taken up by Active Organ 3, and $O_2$ of the $I_2$ radioisotope counts are not taken up by Active Organ 3, and thus, output from Active Organ 3. The sum of the $O_1$-$O_3$ radioisotope counts respectively output from Active Organs 1-3 and input into Active Organ 4 as $I_{4+}$ radioisotope counts. $K_4$ of the $I_4$ radioisotope counts and $I_{4+}$ radioisotope counts are taken up by Active Organ 4, and $O_4$ of the $I_4$ radioisotope counts and $I_{4+}$ radioisotope counts are not taken up by Active Organ 4, and thus, output from Active Organ 4 to the Heart.

After the radioisotope counts $K_1$-$K_4$ and concentrations $C_1$-$C_4$ have been obtained from the acquired image data for Active Organs 1-4 by accumulating radioscope counts in and sampling $ROI_1$-$ROI_4$ associated with Active Organs 1-4 in the manner described above, and the total $I_0$ radioisotope counts injected into the patient have been obtained by accumulating the total counts in the imaging data, the functional volume indices $fV_1$-$fV_4$ can be respectively computed for Active Organs 1-4 in accordance equations [7], [8], [23], and [31] above, while the individual function indices $F_1$-$F_4$ can be respectively computed for Active Organs 1-4 in accordance with equations [9], [10], [24], and [32] above.

Based on the previously described premise that the $I_0$ radioisotope counts injected into the patient divides between the radioisotope counts $I_1$-$I_4$ based on the effective flow resistance of Active Organs 1-4, and assuming that all of the $I_0$ radioisotope counts injected into the patient are distributed as radioisotope counts $I_1$-$I_4$, if:

$$fV_0 = fV_1 + fV_2 + fV_3 + fV_4, \qquad [39]$$

where $fV_0$ is the total functional volume index of Active Organs 1-4, $fV_1$ can be computed in accordance with equation [7] above, $fV_2$ can be computed in accordance with equation [8] above, $fV_3$ can be computed in accordance with equation [23], and $fV_4$ can be computed in accordance with equation above, then:

$$I_1 = I_0 * fV_1/fV_0; \qquad [40]$$
$$I_2 = I_0 * fV_2/fV_0; \qquad [41]$$
$$I_3 = I_0 * fV_3/fV_0; \text{ and} \qquad [42]$$
$$I_4 = I_0 * fV_4/fV_0, \qquad [43]$$

where $I_0$ and $fV_1$-$fV_4$ are known values determined above.

The unknown radioisotope counts $O_1$-$O_3$ not taken up and output by Active Organs 1-3 may then be computed by incorporating the values of the radioisotope counts $I_1$-$I_3$ input into Active Organs 1-3 into equations [12]-[13] and [29]. The unknown radioisotope count $O_4$ not taken up and output by Active Organ 4 may be computed by incorporating the value of the radioisotope count $I_3$ and the values of the radioisotope counts O1-O3 input into Active Organ 4 into:

$$O_4 = I_4 - I_{4+} - K_4, \qquad [45]$$

where $I_4$, $I_{4+}$, and $K_4$ are known values determined above. The individual function indices $F_1$-$F_4$ of Active Organs 1-4 may then be computed by incorporating the values of radioisotope counts $O_1$-$O_4$ into equations [9]-[10], [24], and

[32]. The individual organ type indices $\omega_1$-$\omega_4$ respectively corresponding to Active Organs 1-4 can be determined as described above, while the organ reserve indices $R_1$-$R_4$ can be respectively computed for Active Organs 1-4 in accordance with equations [17]-[18], [30], and [38] above.

Figure 10:
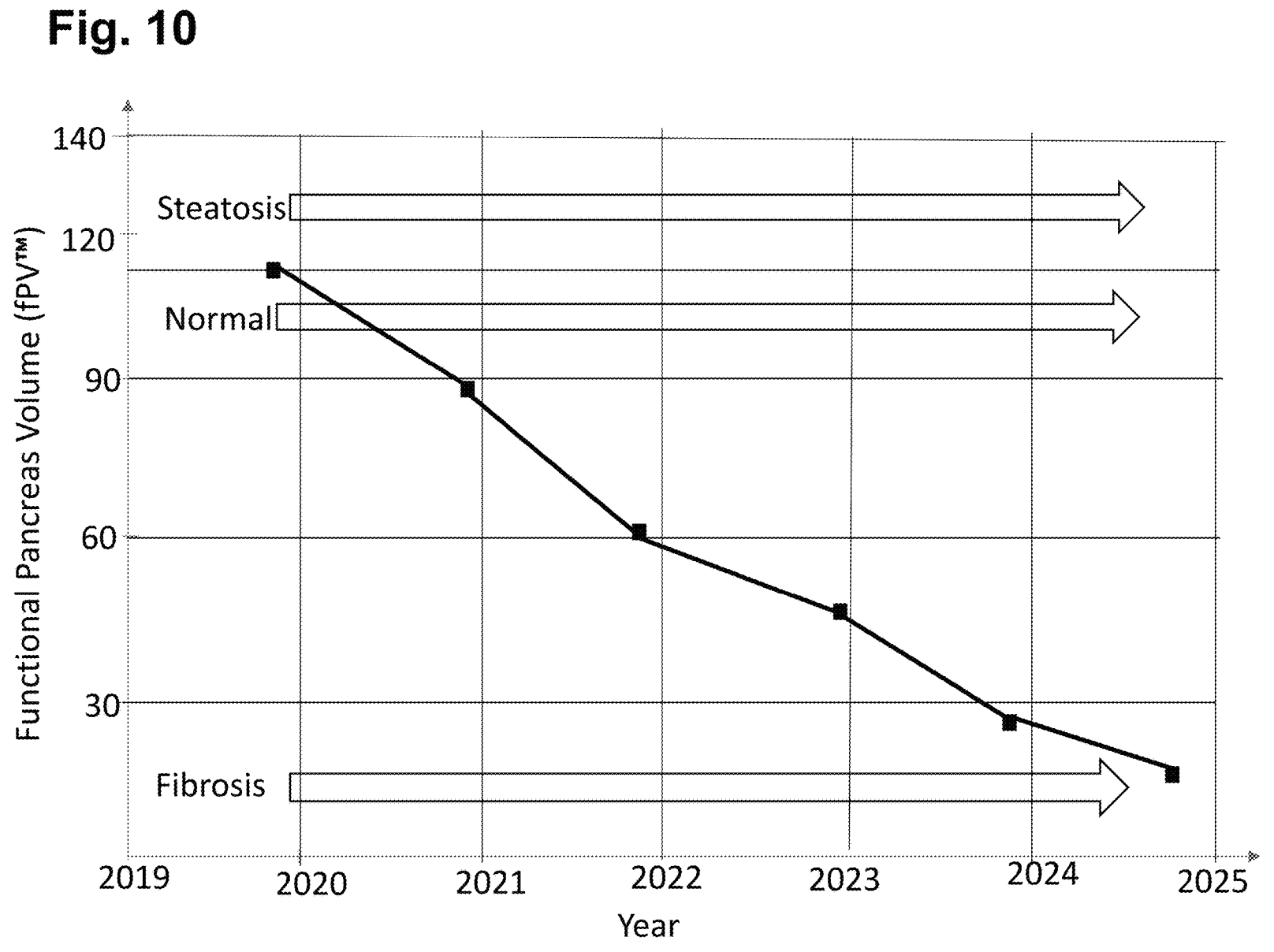
Figure 11:
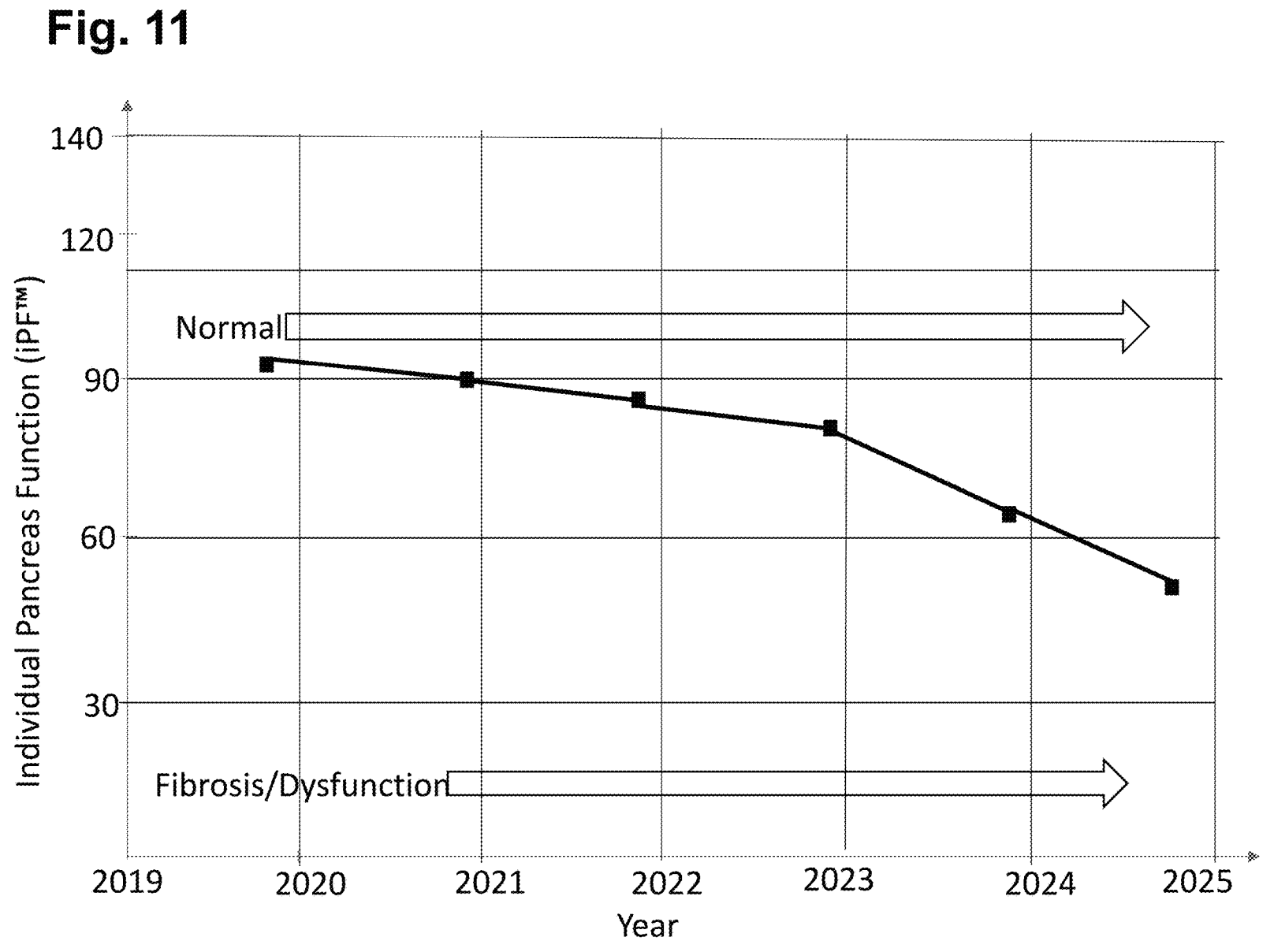

Significantly, the fPV™ index and iPF™ index may be used to stage the health of the pancreas of a patient. In one embodiment, multiple sets of fPV™ indices and iPF™ indices may be generated over a period of time (e.g., several months or even years) and plotted on the differential graph, such that a trajectory of the health of the pancreas may be determined. For example, multiple fPV™ indices may be plotted over time, as illustrated in FIG. 10, while multiple iPF™ indices may be plotted over time, as illustrated in FIG. 11. As can be seen, an extremely high fPV™ index indicates steatosis in the pancreas, a relatively high fPV™ index indicates a normal pancreas with no fibrosis, and a low fPV™ index indicates increasing levels of fibrosis. A relatively high iPF™ index indicates a highly functioning pancreas, while a relatively low iPF™ index indicates increasing levels of fibrosis/dysfunction.

Figure 12:
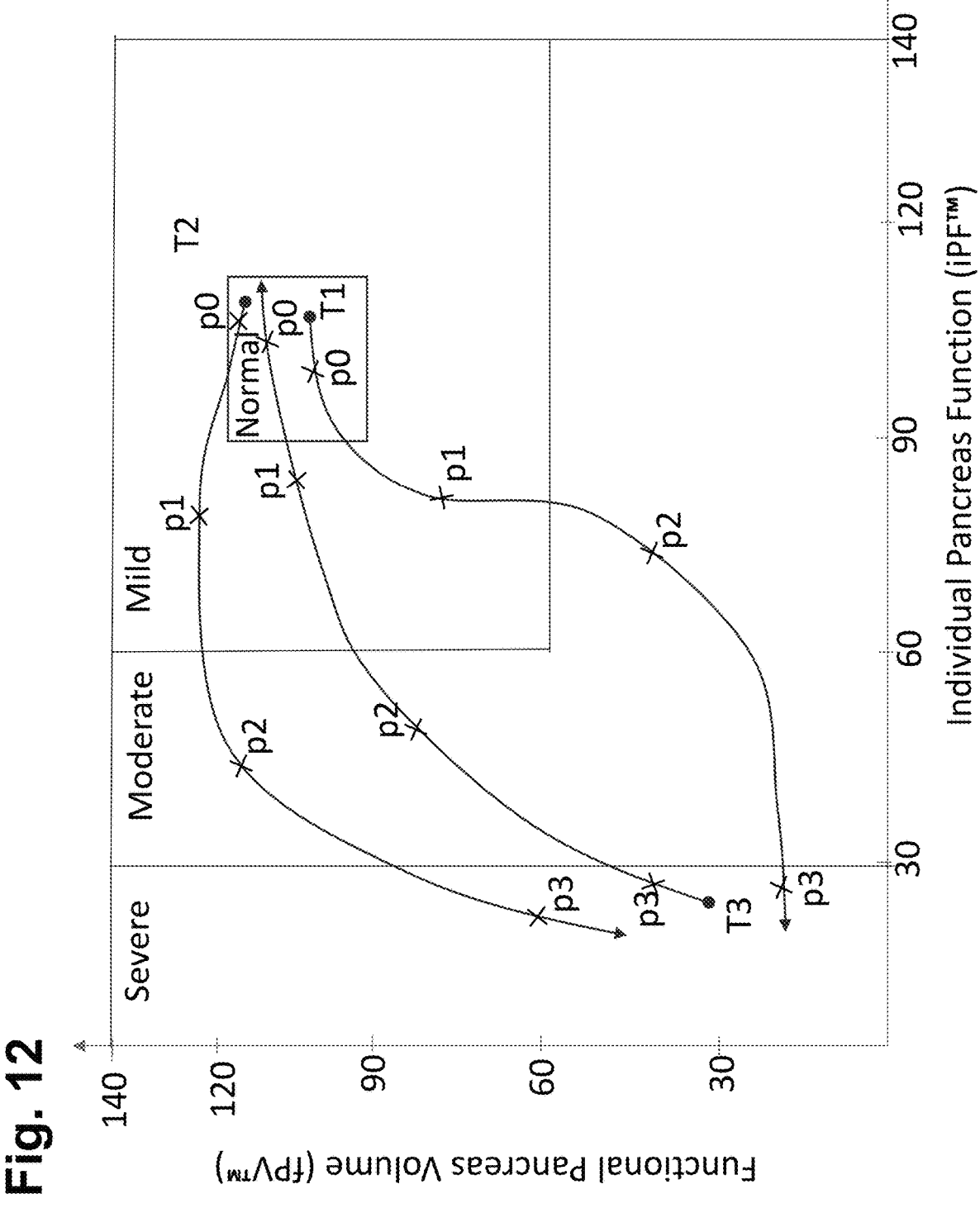
FIG. 12 is a two-dimensional differential graph of three exemplary trajectories of a fPV™ index and a iPF™ index computed by the diagnostic system of FIG. 2.

Significantly, as illustrated in FIG. 12, a two-dimensional differential graph of the fPV™ index (vertical axis) and iPF™ index (horizontal axis) may be generated. In the illustrated embodiment, the pancreas health of the patient may be staged between normal (stage P0), mild (stage P1), moderate (stage P2), and severe (stage P3) by determining the location of the coordinate of the values of fPV™ index and iPF™ index within the regions of the differential graph respectively corresponding to these stages. For example, the coordinate points P0 reside in the region corresponding to the normal stage; the coordinate points P1 reside in the region corresponding to the mild stage; the coordinate points P2 reside in the region corresponding to the moderate stage; and the coordinate points P3 reside in the region corresponding to the severe stage. In the illustrated embodiment, the normal stage indicates that the patient is not suffering from CP, whereas the mild, moderate, and severe stages indicate that the patient is suffering from CP, ranging from mild CP, moderate CP, and severe CP. It should be appreciated, however, that, in alternative embodiments, the number of different stages may be less than four or more than four.

Multiple sets of fPV™ indices and iPF™ indices may be generated over a period of time (e.g., several months or even years) and plotted on the differential graph, such that a trajectory of the function of the pancreas may be determined. This trajectory and the rate of traversal through it provides valuable prognostic information and may be analyzed to predict an outcome for the patient, including both the disease end-point and the time frame for reaching that end-point. For example, as illustrated in FIG. 12, an exemplary trajectory T1 immediately drops from a normal stage along both fPV™ and iPF™ axes until it reaches the severe stage. An exemplary trajectory T2 initially rises from a normal stage along the fPV™ axis (e.g., due to fatty buildup in the pancreas, indicating steatosis of the pancreas), while dropping along the iPF™ axis, and then drops along both of the fPV™ and iPF™ axes (mimicking the exemplary trajectory T1) until it reaches the severe stage. An exemplary trajectory T3 rises from a severe stage along both fPV™ and iPF™ axes until it returns to a normal stage, indicating a recovering patient (possibly due to an effective drug therapy). Different reference trajectories can be coded and labeled into a multitude of disease progression categories, and used for further personalized monitoring and management of the patient. For example, the trajectory of the function of the pancreas of a particular patient may be compared to these reference trajectories, and the patient associated with the disease progression category of the reference trajectory that best matches the actual trajectory of the patient.

It should be noted that the relationship between the fPV™ index and the iPF™ index is logarithmic, with the iPF™ index falling more rapidly than the fPV™ index as the CP progresses, since the fPV™ index reflects the number of functioning pancreatic cells, whereas the iPF™ index represents the product of the number of functioning pancreatic cells and the average cell activity of the pancreas. Cellular abnormalities affect cell activity, which reduces the iPF™ index. As fibrosis increases, the number of non-functioning pancreatic cells increases, reducing both the fPV™ index and the iPF™ index. This is one of the reasons why this analysis technique, which considers both the fPV™ index and the iPF™ index, may outperform conventional imaging techniques, which only detect advanced fibrosis.

Although the differential graph illustrated in FIG. 12 is a two-dimensional graph, in an optional embodiment, a third axis having a iPT™ index may be added to create a three-dimensional differential graph. In this case, the different regions corresponding to the different stages may take the form of a volume as opposed to an area. In this manner, the stages may be standardized to the specific characteristics of the patient, e.g., the gender, age, height, biomarkers, and genetics of the patient. Notably, as the disease progresses from the normal stage towards the severe state, the biomarker of the patient, and thus the iPT™ index, may drop, and in contrast, as the disease reverts back to the normal stage, the biomarker of the patient, and thus, the iPT™ index may rise. As such, multiple iPT™ indices for the patient, along with the fPV™ indices and iPF™ indices, are preferably generated over a period of time.

In one embodiment, instead of, or in addition to, analyzing the fPV™ index, iPF™ index, and iPT™ index in the context of a differential graph, the iPR™ index, which is based on the fPV™ index, iPF™ index, and iPT™ index in accordance with equation [7] above, can be considered. For example, the ability of the pancreas to maintain its physiologic function in the face of disease, injury, surgery or interventional procedure will be deemed to increase as the iPR™ index increases, and will be deemed to decrease as the iPR™ index decreases.

Referring now to FIGS. 13-17, a mouse study was performed to validate the afore-mentioned pancreatic health staging technique. In particular, three initially healthy mice (2A, 3A, 4A) were injected with cerulein over six weeks to induce CP in the mice, while a fourth mouse was treated as a control and not injected with cerulein. Histology confirmed that the control mouse was unaffected and remained healthy, while the other three mice 2A, 3A, 4A developed advanced CP. Prior to injection with cerulein and six weeks after continued injection with cerulein, the three mice 2A, 3A, 4A were injected with the zinc-chelating imaging probe (ZCIP) labeled with 99mTc radioisotope and imaged using SPECT scanner to collect baseline data and post-cerulein data, including fPV™ indices and iPF™ indices, from the mice 2A, 3A, 4A. As shown in FIG. 13, the spleen, pancreas, and kidneys of a mouse are active organs that take up the ZCIP, and are thus, imaged to collect the relevant baseline and post-cerulein data. It should be appreciated that in future mouse studies, the liver, as an active organ that takes up the ZCIP, and the bladder, which serves as a reservoir for the ZIP after being filtered by the kidneys, may be imaged to collect relevant baseline and post-cerulein data.

Figure 14:
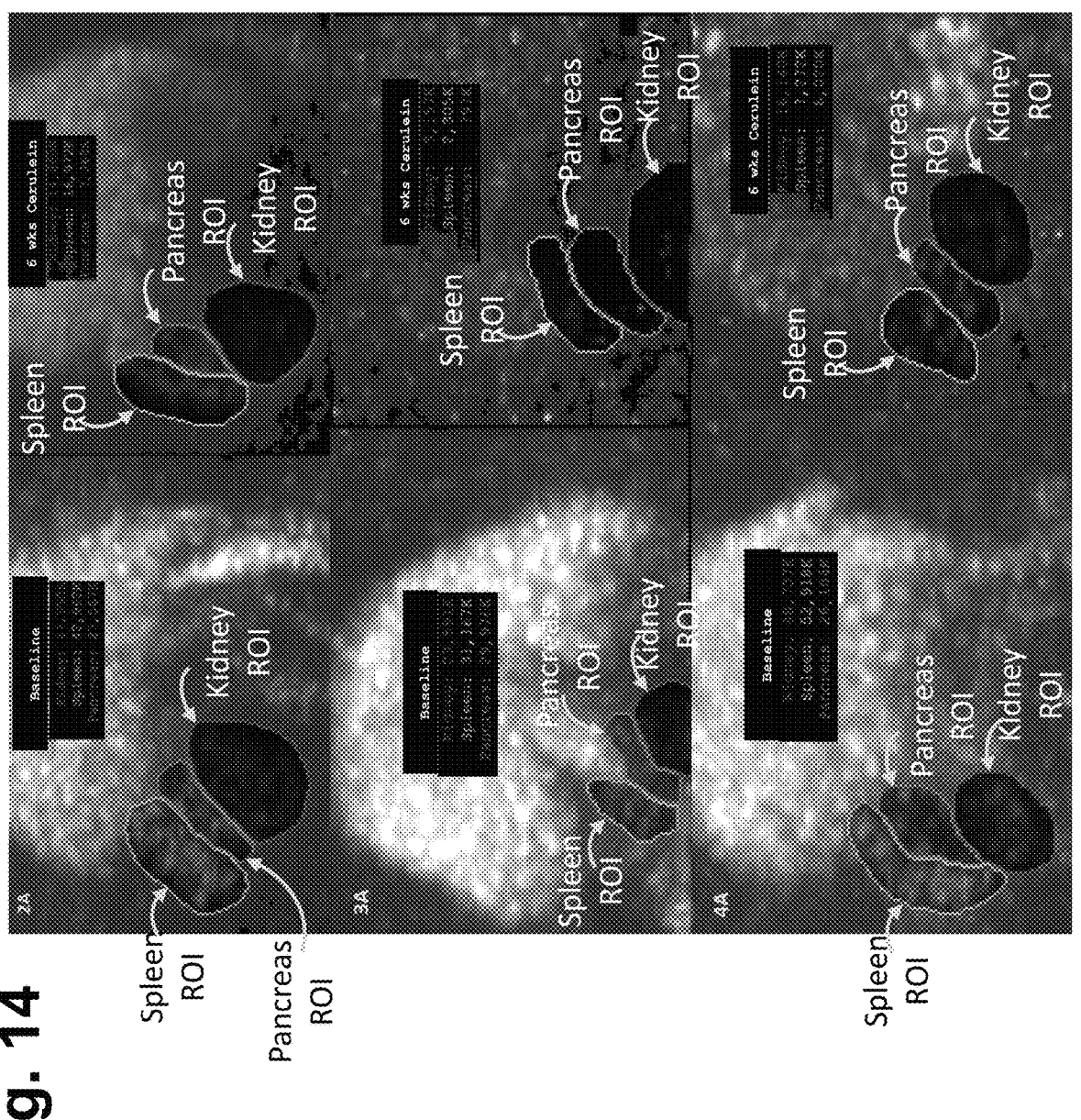
FIG. 14 is image data acquired from three mice 2A, 3A, 4A, particularly showing regions of interest (ROIs) associ-

As illustrated in FIG. 14, ROIs corresponding to the spleen, pancreas, and kidneys were manually drawn by a single person using the same method. Both transaxial and coronal views from the SPECT scanner were used to validate the ROIs. The liver (the large mass at the top of the image) was used to verify the location of the two kidneys. The kidneys were used to pinpoint the spleen and the pancreas. The ROIs were colorized and software was used to accumulate the radioisotope counts K in each ROI associated with the kidneys, spleen, and pancreas.

For Mouse 2A, pancreas radioisotope counts K dropped from 23.6M to 7.4M, representing a 60% drop from baseline. For Mouse 3A, the pancreas radioisotope counts K dropped from 30.0M to 0.8M, representing a 97% drop from baseline. Thus, Mouse 3A was far more impaired by the cerulein than Mouse 2A. For Mouse 4A, the pancreas radioisotope counts K dropped from 26.1M to 6.0M, representing a 77% drop from baseline. Mouse 4A was more impaired by the cerulein than Mouse 2A, but less impaired by the cerulein than Mouse 3A. The pancreas radioisotope counts K at baseline and post-cerulein were used to compute fPV™ indices and iPF™ indices for Mouses 2A, 3A, 4A. Notably, the iPF™ indices for Mouses 2A, 3A, 4A were computed in accordance with the organ configuration model illustrated in FIG. 9. As illustrated in FIG. 15, the fPV™ indices and iPF™ indices quantified individual differences between Mouses 2A, 3A, 4A, something not easily done with tests that do not have quantitative function and volume indices. The fPV™ indices, on average for Mouses 2A, 3A, 4A, decreased by 47%, while the iPF™ indices, on average for Mouses 2A, 3A, 4A, decreased by 82%. This result (i.e., the additional decrease in the iPF™ indices relative to the fPV™ indices) is expected, since the fPV™ index reflects fibrosis in the pancreas, while the iPF™ index reflects both average cell activity (dysfunction) and fibrosis in the pancreas.

Notably, cerulein causes inflammation in other organs, including the liver, kidneys and spleen, such that the radioisotope counts K in these organs drop from their baseline levels to their post-cerulein levels, as illustrated in FIG. 14. Those skilled in the art would know that full implementation of calibration for fPV™ and standardization for iPF™ would reduce the dispersion of the fPV™ index and iPF™ index computations at baseline for healthy mice. It is expected that the dispersion for both of the fPV™ index and iPF™ index computations between different mice would tighten to 1.00±0.05 or less. Those skilled in the art would know that scatter and attenuation image corrections may be used to tighten these dispersions further as needed.

As illustrated in FIG. 16, the computed baseline and post-cerulein fPV™ index and iPF™ index for each of Mouses 2A, 3A, 4A were plotted on a differential graph, and a logarithmic trajectory fitted to the coordinates of the fPV™ indices and iPF™ indices. As illustrated in FIG. 17, a mathematical Monte Carlo simulation model was constructed using the data acquired from Mouses 2A, 3A, 4A to obtain stages of the fPV™/iPF™ indices over a 6-week range. Baseline data acquired from Mouses 2A, 3A, 4A, and some reasonable assumptions on calibration and standardization, were used to simulate a stage of fPV™/iPF™ coordinates associated with a normal function (stage P0). End stage data acquired from Mouses 2A, 3A, 4A 6 weeks after initial injection of the cerulein were used to simulate a stage of fPV™/iPF™ coordinates associated with severe dysfunction (stage P3). Stages of fPV™/iPF™ coordinates associated with mild dysfunction (stage P1) and moderate dysfunction (stage P2) were interpolated from the stages of fPV™/iPF™ coordinates associated with normal function (stage P0) and severe dysfunction (stage P3). It should be appreciated that stage P0 represents no CP, whereas stages P1-P3 represent increasing levels of CP. True positive/negative and false positive/negative rates were determined and sensitivity and specificity calculated. Based on many simulations, the model predicts a specificity of 0.98 and sensitivity of 0.99 for differentiation of CP from normal. One reason for such high specificity and high sensitivity is that the CP staging is performed using two metrics-fPV™ index and iPF™ index.

Having described the diagnostic system 10, one method 200 of using the diagnostic system 10 to diagnose and treat a patient with CP will now be described with respect to FIG. 18.

In a preferred embodiment, the patient is injected with a radioisotope solution targeting an organ of interest, and in this case, with ZCIP labeled with Technetium$^{99m}$ to target the pancreas of the patient (step 201). Next, SPECT/CT image data of the pancreas and other organs (including the vertebral bodies, liver, spleen, kidneys, and bladder), is acquired from the patient using the image scanner 12 (step 202). It should be understood that the image scanner 12 may be operated to acquire image data from a planar, anterior, posterior, oblique, sagittal, and/or coronal views. The image data may be "static" or "dynamic." Dynamic image data is a series of M sequential SPECT images taken at relatively short durations of $\Delta T$ each. A static image is essentially an average of all M images taken over a duration of $M*\Delta T$ with the appropriate corrections made for decay and scatter during the scan. The image data may be raw image data acquired by the image scanner or may be reformatted image data, secondary captured data, or derived image data. Preferably, the acquired image data may be in a Digital Imaging and Communications in Medicine (DICOM) format. The acquired image may be stored on the image scanner 12 and transferred to the PACS 16 for long-term storage. The image data stored on the PACS 16 may or may not be encrypted.

Next, the workstation 14 retrieves the image data from PACS 16 using the PACS interface module 28 of the diagnostic software 20 (step 203). In one embodiment, the image data is retrieved from the PACS 16 using the DICOM protocols, although other protocols could be used. Although retrieving image data from the PACS 16 is preferred, in alternative methods, it should be understood that the image data may be retrieved directly from the image scanner 12 or from some other archival device, such as a CD, DVD, USB stick, etc., installed on the work station 14 or from a remote storage device via a network or internet (cloud). It should also be understood that the image data may be automatically or manually transmitted from PACS 16, image scanner 12 or archival device to the workstation 14 rather than being retrieved by the workstation 14 from the PACS 16, image scanner 12, or archival device.

Next, the workstation 14 retrieves patient data (e.g., patient data, demographics, clinical indications, medications, history, laboratory results, genetics, physician orders, etc.) from the EHR 18 using the EHR interface module 30 of the diagnostic software 20 (step 204). In a preferred method, the patient data is retrieved from the EHR 18 using the HL/7 protocols, although other protocols could be used. Although retrieving patient data from the EHR 18 is preferred, it should be understood that the patient data may be retrieved directly from the patient or from some other information source. Also, it should be understood that the patient data may be automatically or manually transmitted from the EHR 18 or other source of information to the workstation 14 rather than being retrieved by the workstation 14 from the EHR 18 or other source of information.

Next, image analyzer module 32 of the diagnostic software 20 analyzes the retrieved image data and the retrieved patient data, and determines various pancreas health indices, including the functional pancreas volume (fPV™) index, the individual pancreas function (iPF™) index, individual pancreas type (iPT™) index, and individual pancreas reserve (iPR™) index from the retrieved image data and retrieved patient data (step 205). In one method, organs, such the pancreas, liver, spleen, kidneys, and bladder, as well as the vertebral bodies, are automatically identified by using SPECT/CT. In particular, the CT image data provides high spatial resolution, and so can be used to locate the organs, while the SPECT image data is registered on the CT image data, the organs are identified, and ROIs are automatically drawn around the organs. The radioisotope counts can be accumulated for each of the ROIs, and the fPV™ index, iPF™ index, and iPR™ index computed from the radioisotope counts in accordance with the appropriate equations above. The iPT™ index may be determined from the patient data.

Next, the image analyzer module 32 of the diagnostic software 20 stages the function of the pancreas based on the determined fPV™ index, iPF™ index, and iPT™ index (e.g., normal function (P0), mild dysfunction (P1), moderate dysfunction (P2), and severe dysfunction (P3)) (step 206). Coordinates of the fPV™ index and iPF™ index may be plotted on a two-dimensional differential graph (or the fPV™ index, iPF™ index, and iPT™ index on a three-dimensional differential graph) to facilitate the pancreas staging function. Steps 201-206 may be repeated over a period of time (e.g., several months or years), to determine sets of health indices and pancreas staging. The image analyzer module 32 of the diagnostic software 20 may determine the trajectory of the function of the pancreas based on the sets of health indices.

At any time after step 206, the image analyzer module 32 of the diagnostic software 20 may generate and distribute a comprehensive report (step 207). As illustrated in FIG. 19, such report may include the auxiliary information, the health indices, including fPV™ index, iPF™ index, and iPT™ index, and iPR™ index, patient trajectory and traversal rate, and disease progression category, including stage of the pancreas, and image data. The reporting module 34 may send the report to the workstation 14 (which may display the report on the user interface 26), send the report to the PACS 16 via the PACS interface module 28, and/or send the report to the EHR 18 via the EHR interface module 30.

Lastly, the patient may be appropriately treated based on the comprehensive report (step 208). Significantly, the comprehensive report may be used as a clinical standard of care that assists clinicians with patient triage, resulting in improved overall disease management. For patients that are suffering from suspected pancreatic dysfunction, the diagnostic software 20 will advance clinical diagnostic staging across the disease spectrum. By expediting detection and diagnostic timelines, the diagnostic software 20 will provide more opportunities to implement treatment strategies in patients at earlier stages of pancreatic disease. Through these mechanisms, the use of the diagnostic software 20 will impact both the health and quality of life outcomes for patients suffering from pancreatic disease, thereby reducing hospitalization and mortality. Treatments for chronic pancreatitis include medications to relieve pain, pancreatic enzyme replacement, insulin for diabetics, and antibiotics if infection occurs. Abstinence from alcohol and smoking, dietary changes and weight loss also help. ERCP to remove stones from the pancreatic ducts, pseudocyst drainage to remove excess fluids, partial or full pancreatic resection, and stem cell transplantation are other interventions, The earlier diagnosis will stratify and triage patients for medications to delay or retard progression of pancreatic disease. For instance, physicians could start patients on treatments for complications. In addition, newer medications, such as anti-fibrotics, are now in clinical trials for altering and/or slowing pancreatic disease. Earlier detection of pancreatic disease will be an advantage by providing opportunities for identification of patients earlier in the progression of disease. If major surgery or other interventional procedure is being considered (e.g., for cancer), the iPR™ index may be used to determine if the pancreas has a sufficient reserve for tolerating such surgery or procedure.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A diagnostic method of determining a health condition of an organ of a patient, comprising:
   administering a radioisotope dose to the patient, such that the organ uptakes the radioisotope and one or more other organs uptake the radioisotope;
   acquiring imaging data via nuclear medicine imaging from the patient when the radioisotope dose is active in the patient;
   deriving a radioisotope count uptaken by the organ and a radioisotope uptaken by one or more other organs from the acquired image data;
   determining a radioisotope count perfused into the organ based on the derived radioisotope count uptaken by the organ and the derived radioisotope uptaken by the one or more other organs;
   determining a functional organ volume index;
   determining an individual organ function index by computing a quotient of the derived radioisotope count uptaken by the organ over the derived radioisotope count perfused into the organ;
   staging a health of the organ based on the determined functional organ volume index and the determined individual organ function index; and
   communicating the staged health of the organ to a clinician.

2. The diagnostic method of claim 1, wherein determining the functional organ volume index comprises deriving a concentration of the radioisotope in the organ from the acquired image data, and computing a product of the derived radioisotope count of the organ and a volume of a voxel of the image data divided by the derived concentration of the radioisotope in the organ.

3. The diagnostic method of claim 1, further comprising generating a differential graph of the functional organ volume index and the determined individual organ function index, wherein a health of the organ is staged based on a location of a coordinate of the determined functional organ volume index and the determined individual organ function index within one of a plurality of regions of the differential graph.

4. The diagnostic method of claim 1, wherein staging the function of the organ comprises selecting one of a plurality of different stages.

5. The diagnostic method of claim 4, wherein the plurality of different stages comprises a normal stage and at least one stage of decreased health.

6. The diagnostic method of claim 5, wherein the at least one stage of decreased health comprises a mild decreased health stage, a moderate decreased health stage, and a severe decreased health stage.

7. The diagnostic method of claim 1, further comprising:
   repeating the radioisotope administering, image data acquisition, and acquired image data analyzing steps to determine a plurality of functional organ volume indices and plurality of individual organ function indices;
   generating a differential graph of the determined plurality of functional organ volume indices and the determined plurality of individual organ function indices;
   determining a trajectory based on locations of coordinates of the determined plurality of functional organ volume indices and the determined plurality of individual organ function indices in the differential graph;
   determining an organ disease prognosis of the patient based on the determined trajectory; and
   communicating the determined organ disease prognosis to the clinician.

8. The diagnostic method of claim 1, further comprising:
   determining an individual organ reserve index from the determined functional organ volume index and the determined individual organ function index; and
   communicating the determined individual organ reserve index to the clinician.

9. The diagnostic method of claim 8, wherein determining the individual organ reserve index comprises computing a product of the determined functional organ volume index and the determined individual organ function index.

10. The diagnostic method of claim 1, wherein the image data is acquired using a functional scanner.

11. The diagnostic method of claim 1, wherein the radioisotope is Technetium$^{99m}$.

12. The diagnostic method of claim 1, wherein the organ is a pancreas, the functional organ volume index is a functional pancreas volume index, and the individual organ function index is an individual pancreas function index.

13. A method of treating a patient having chronic pancreatitis (CP), comprising:
   performing the diagnostic method of claim 12, wherein the health of the pancreas is staged as having CP; and
   treating the CP of the pancreas based on the staged health of the pancreas.

14. A diagnostic method of determining a health condition of an organ of a patient, comprising:
   administering a radioisotope dose to the patient, such that the organ uptakes the radioisotope;
   acquiring imaging data via nuclear medicine imaging from the patient when the radioisotope dose is active in the patient;
   deriving a radioisotope count uptaken by the organ and a radioisotope uptaken by one or more other organs from the acquired image data;
   determining a radioisotope count perfused into the organ based on the derived radioisotope count uptaken by the organ and the derived radioisotope uptaken by the one or more other organs;
   determining a functional organ volume index;
   determining an individual organ function index by computing a quotient of the derived radioisotope count uptaken by the organ over the derived radioisotope count perfused into the organ;

computing a product of the determined functional organ volume index and the determined individual organ function index;

deriving an individual organ reserve index from the product of the determined functional organ volume index and the determined individual organ function index; and communicating the derived individual organ function index to a clinician.

15. The diagnostic method of claim 14, wherein determining the functional organ volume index comprises deriving a concentration of the radioisotope in the organ from the acquired image data, and computing a product of the derived radioisotope count of the organ and a volume of a voxel of the image data divided by the derived concentration of the radioisotope in the organ.

16. The diagnostic method of claim 14, wherein the organ is a pancreas, the functional organ volume index is a functional pancreas volume index, the individual organ function index is an individual pancreas function index, and the individual organ reserve index is an individual pancreas reserve index.

17. A method of treating a patient having chronic pancreatitis (CP), comprising:

performing the diagnostic method of claim 16, wherein the derived individual organ reserve index indicates CP of the pancreas; and treating the CP of the pancreas based on the derived individual organ reserve index.

18. The method of claim 17, wherein the patient has cancer, and the method further comprises treating the cancer based on the derived individual organ reserve index.

19. A diagnostic method of determining a health condition of an organ of a patient, comprising:

administering a radioisotope dose to the patient, such that the organ uptakes the radioisotope;

acquiring imaging data via nuclear medicine imaging from the patient when the radioisotope dose is active in the patient;

analyzing the acquired image data to determine a functional organ volume index and an individual organ function index;

generating a differential graph of the functional organ volume index and the determined individual organ function index;

staging a health of the organ based on a location of a coordinate of the determined functional organ volume index and the determined individual organ function index within one of a plurality of regions of the differential graph; and communicating the staged health of the organ to a clinician.

20. A diagnostic method of determining a health condition of an organ of a patient, comprising:

administering a radioisotope dose to the patient, such that the organ uptakes the radioisotope;

acquiring imaging data via nuclear medicine imaging from the patient when the radioisotope dose is active in the patient;

analyzing the acquired image data to determine a functional organ volume index and an individual organ function index;

repeating the radioisotope administering, image data acquisition, and acquired image data analyzing steps to determine a plurality of functional organ volume indices and plurality of individual organ function indices;

generating a differential graph of the determined plurality of functional organ volume indices and the determined plurality of individual organ function indices;

determining a trajectory based on locations of coordinates of the determined plurality of functional organ volume indices and the determined plurality of individual organ function indices in the differential graph;

determining an organ disease prognosis of the patient based on the determined trajectory; and communicating the determined organ disease prognosis to the clinician.

* * * * *